United States Patent
Russell et al.

(10) Patent No.: US 6,579,685 B1
(45) Date of Patent: *Jun. 17, 2003

(54) METHOD AND APPARATUS FOR SCREENING MICROSCOPIC CELLS UTILIZING LIGHT SCATTER TECHNIQUES

(75) Inventors: Thomas Russell, Miami, FL (US); James Carey Hudson, Miami, FL (US); Wallace H. Coulter, Miami Springs, FL (US); Carlos M. Rodriguez, Miami, FL (US); Constance Mary Hajek, Miami Lakes, FL (US)

(73) Assignee: Coulter International Corp., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/303,924

(22) Filed: Sep. 9, 1994

Related U.S. Application Data

(63) Continuation of application No. 07/617,075, filed on Nov. 23, 1990, now abandoned.

(51) Int. Cl.[7] ................................. G01N 33/53

(52) U.S. Cl. ..................... 435/7.24; 422/73; 422/82.08; 436/172; 436/805; 436/824; 436/825; 435/808; 435/962

(58) Field of Search ................................ 422/73, 82.08; 436/172, 805, 824, 825; 435/808, 962

(56) References Cited

U.S. PATENT DOCUMENTS

| | | | |
|---|---|---|---|
| 4,747,685 A | | 5/1988 | Suzuki ........................ 356/39 |
| 5,125,737 A | * | 6/1992 | Rodriguez et al. |
| 5,223,398 A | * | 6/1993 | Kortright et al. |
| 5,231,005 A | * | 7/1993 | Russell et al. |

* cited by examiner

*Primary Examiner*—Bao-Thuy L. Nguyen
(74) *Attorney, Agent, or Firm*—Warren W. Kurz; Mitchell E. Alter

(57) ABSTRACT

A method for performing screening of one or more cell groups of interest obscured by a cell population such as one or more subsets of interest of a WBC population utilizing at least one light sensing parameter. The cell group of interest is enumerated by utilizing microspheres having monoclonal antibodies bound thereto to modify the sensed characteristics of specified cells to differentiate the cell group of interest from the obscuring cell population.

11 Claims, 26 Drawing Sheets

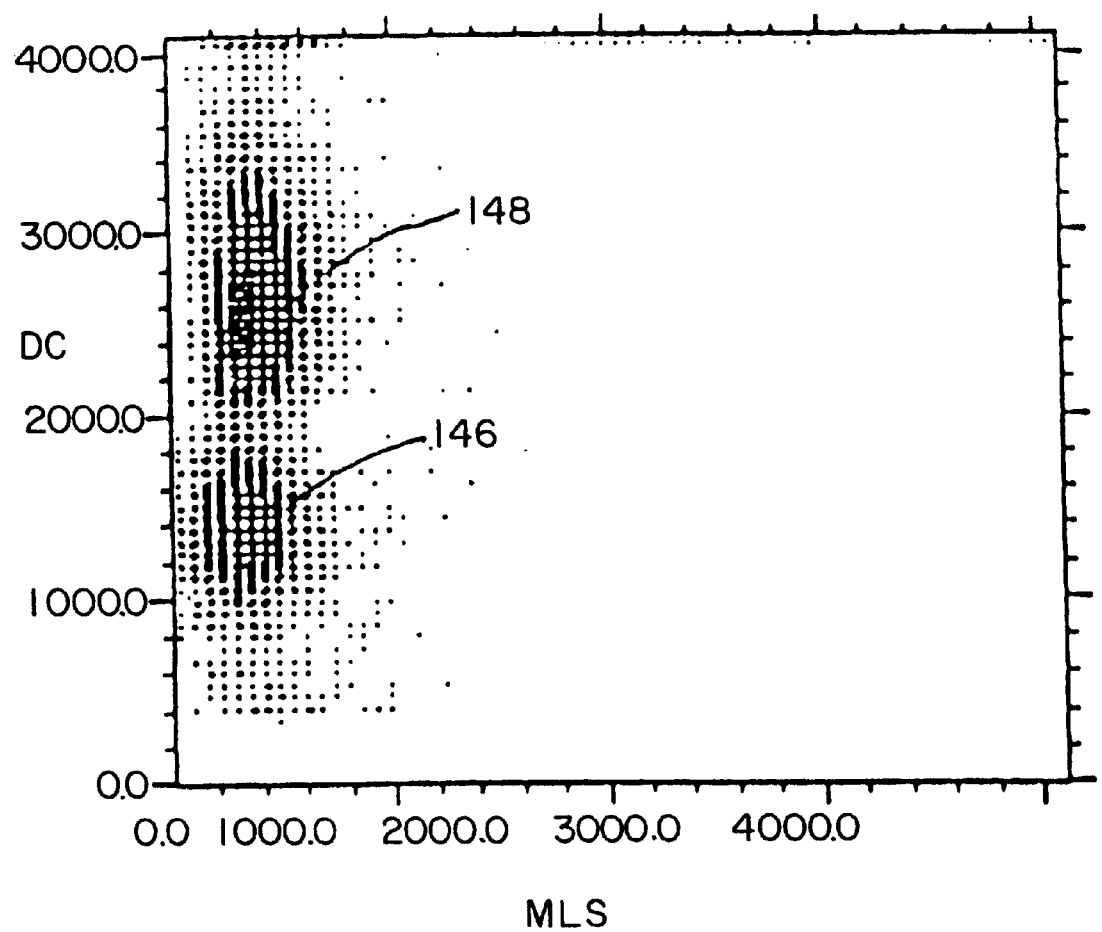

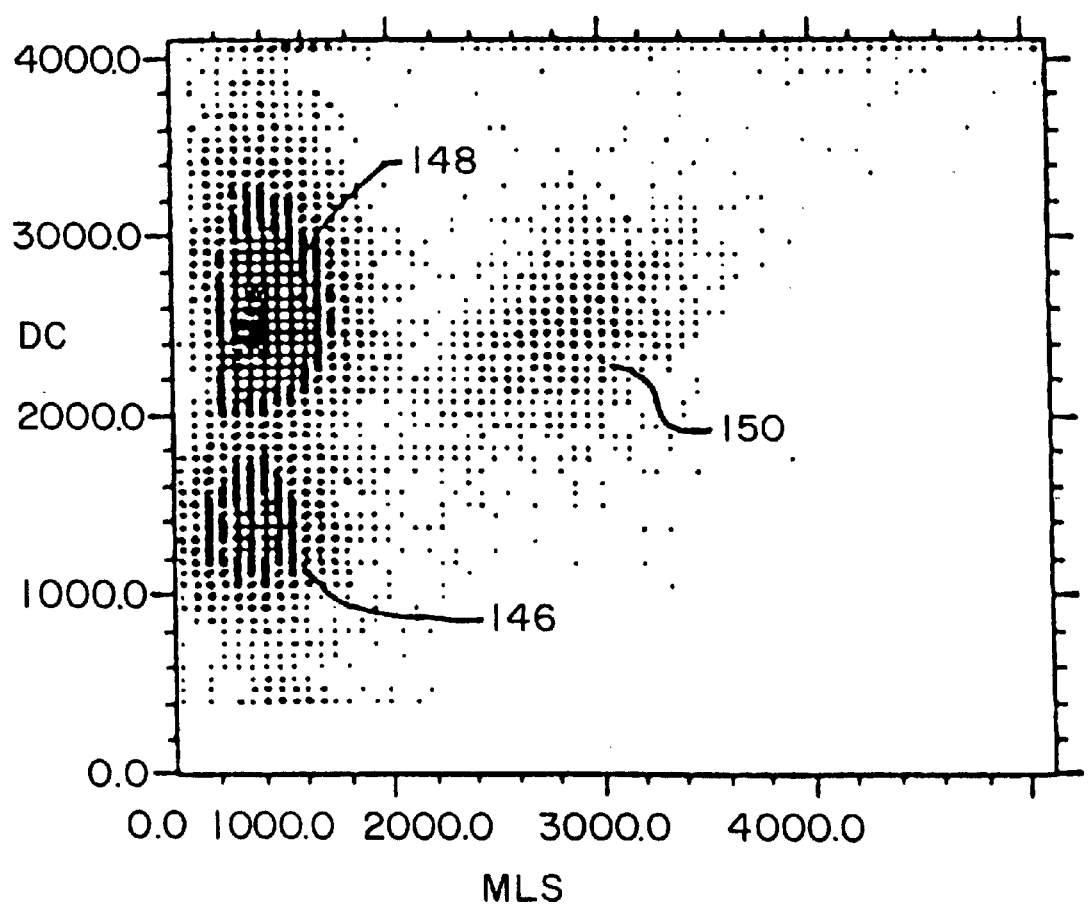

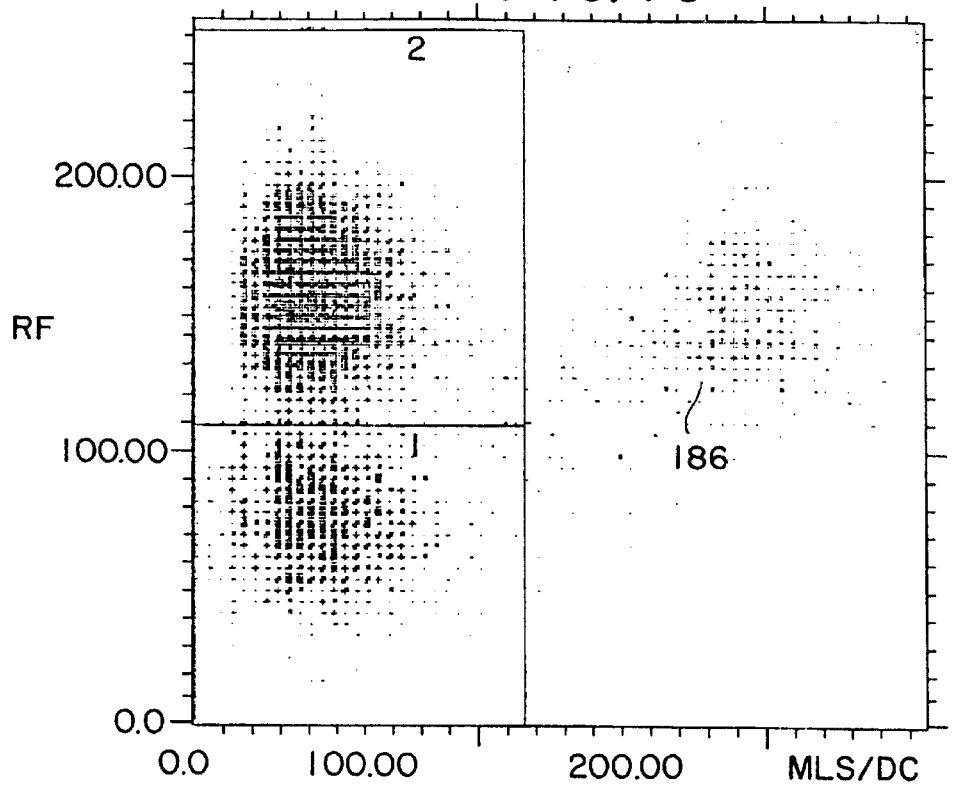
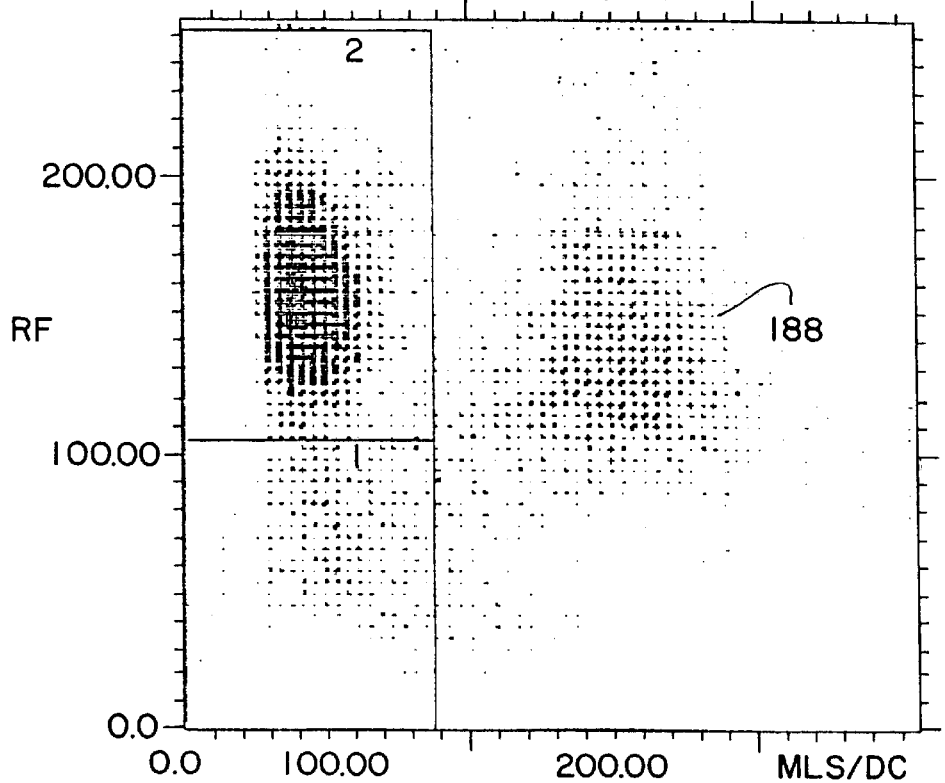

METHOD AND APPARATUS FOR SCREENING MICROSCOPIC CELLS UTILIZING LIGHT SCATTER TECHNIQUES

This is a continuation of application Ser. No. 07/617,075 filed Nov. 23, 1990, now abandoned.

BACKGROUND OF THE INVENTION

This invention relates generally to a method and apparatus for screening microscopic cells which express selected characteristics utilizing light scatter or light scatter and electronic sensing techniques. More particularly, the invention is directed to an analysis of one or more cell groups of interest obscured in a cell population by utilizing microspheres having monoclonal antibodies bound thereto to change the sensed characteristics of each specified cell to differentiate the cells of the cell group of interest from the cell population.

This invention relates generally to an automated analyzer and methods of using same for screening biological cells or formed bodies for the enumeration of populations which express selected characteristics for research, diagnostic, medical or industrial purposes. More particularly, the automated analyzers and methods embodying the invention enable multiple part classifications of cells and formed bodies, functional phenotyping of cells and formed bodies, typing of leukemic, lymphoma and solid tumor cells, among others, using a unique combination of optical or optical and electronic technology and the specificity of selective biological molecules, such as antibodies, for such screening and selective enumeration of the cells and formed bodies.

Automation of routine complete blood cell (CBC) analysis of human peripheral blood by an automated blood cell counter was successfully achieved by the COULTER COUNTER (registered trademark) Model A of Coulter Electronics, Inc. of Hialeah, Fla. The electronic particle sensing system principle of that instrument is disclosed in U.S. Pat. No. 2,656,508 issued Oct. 20, 1953 to Wallace H. Coulter. This Coulter sensing principle was developed and expanded into more sophisticated instrumentation such as the COULTER COUNTER (registered trademark) Model S types of instruments which enabled CBC parameters, absolute cell counts, platelet count and morphology, red blood cell (RBC) morphology, interpretation of normal and abnormal blood specimens by specific computer programs.

The Coulter electronic particle sensing principle employs an aperture sensing circuit using a direct current (DC) aperture supply. Such particle sensors are simple in structure, extremely rugged and reliable as attested to by the substantially universal acceptance of the COULTER COUNTER (registered trademark) automated analyzer in clinical laboratories in the United States and throughout the rest of the World. An improvement in this basic aperture sensing circuit was disclosed in U.S. Pat. No. 3,502,974 issued in 1970 to Wallace Coulter and Walter Hogg. In addition to the standard direct current aperture supply, a high frequency aperture current was applied which enabled the sensing of an additional parameter for classification purposes. The high frequency aperture current produced a signal which is the function of the blood cell's internal conductivity as well as its volume. The signal produced simultaneously by the direct current aperture circuit is a conventional DC amplitude signal which provides an indication primarily of cell volume. The radio frequency amplitude is divided by the direct current pulse amplitude employing a high speed divider circuit to obtain a quotient which is a function of cell volume and internal resistance, conveniently referred to as "opacity". This principle is further described in U.S. Pat. No. 3,502,973 also issued to Wallace Coulter and Walter Hogg, in 1970. The opacity parameter has applicability in cell classification systems. Either a single or a pair of separate apertures could be utilized for this purpose.

Classification of different populations is accomplished by collating the data of the signal pairs as they are produced; one, a measure of particle volume and the other a measure of cell internal resistivity or opacity. A convenient form of presenting this data is by two-dimensional plots referred to as scatterplots or scattergrams. Such plots are well described in *Flow Cytometry and Sorting,* page 371; edited by Melamed Melaney, and Medelsohn, 1979, John Wiley & Sons, NY, N.Y.

Initial applications of the Coulter electronic particle sensing principle was to perform red blood cell counts and then, more sophisticated determinations of other red blood cell parameters. By removing red blood cells from whole peripheral blood, analysis of the white blood cell (WBC) populations could be undertaken so long as the red blood cell removal did not significantly impair properties of the remaining white blood cell populations sought to be measured. Red blood cell lysing reagents were developed for this purpose which, though useful and widely applied, were not entirely satisfactory in all respects for subsequent white blood cell determinations.

Previous methods of flow analysis of leukocytes using DC volume alone or light scatter at various angles have shown three clusters of leukocytes corresponding to lymphocytes, monocytes and granulocytes which included the neutrophil, basophil and eosinophil populations. A rough but useful estimation of eosinophil concentration can be made on some samples. The fifth major population, basophils, is relatively too small for this approach.

Immunologic studies also are important when anomalies are found on a peripheral blood smear. It is necessary to determine the specific subtype of the leukemia in order to better select a treatment method for the disease and to provide the patient with as specific a prognosis as possible. For example, in forms of acute leukemia, there is a predominance of blasts in the peripheral blood. These immature cells can be difficult to classify as either lymphocytic or granulocytic because of the lack of differentiation. If the blast subpopulation that is rapidly proliferating is found to be T11 receptor bearing, the leukemia can be classified as an acute lymphoblastic leukemia, T-cell type. In general, T lineage ALL has a poorer prognosis than B lineage ALL. Further subgrouping these leukemias according to their level of differentiation is also customary. Groups I and II exhibit antigens that are seen on early thymic precursor cells; while those expressed in Group III are similar to the surface antigens found on mature T cells. Information such as this regarding the surface antigens expressed on leukemic cells is useful for patient prognosis and treatment.

Immunology experiments were first developed utilizing a light microscope for determination of lymphocyte subsets. Rosette formation between human lymphocytes and sheep red blood cells was observed by Coombs and others in 1970. Later studies found that all or at least a major portion of thymus-derived lymphocytes (T-cells) under the proper conditions displayed the rosette formation phenomenon. These studies utilized Ficoll isolated lymphocytes and were for a period of time routinely employed for subset classification of isolated lymphocytes utilizing a light microscope.

Lymphocyte subsets now conventionally are determined by fluorescent labeling of the cells, in a sample with a fluorescent-tagged monoclonal antibody. The fluorescent-tagged monoclonal antibody binds to the antigen of interest on the surface of the cells expressing the antigen. The cell sample then is analyzed by utilizing a fluorescent microscope or by utilizing a highly sophisticated flow cytometry instrument. When utilizing a flow cytometry instrument, the cell sample preparation, data collection and data analysis must be performed by a specially trained technician. The flow cytometry instrument includes a laser and complex optical system, a high-power computer and electrical and fluidic systems. The component systems of the flow cytometry instrument must be properly maintained and calibrated on a regular and frequent basis. Although the flow cytometry instrument currently is the reference lymphocyte subset determination method, the method has several drawbacks including the high cost of the instrument and the expertise required to correctly operate such instrument.

Lymphocyte subsets also can be determined utilizing automated instruments and methods developed by the assignee of the present application, Coulter Corporation. An improved simple automated instrument and methods of using the same is disclosed in application U.S. Ser. No. 587,646, filed Sep. 20, 1990, now U.S. Pat. No. 5,223,398 entitled AUTOMATED ANALYZER AND METHOD FOR SCREENING CELLS OR FORMED BODIES FOR ENUMERATION OF POPULATIONS EXPRESSING SELECTED CHARACTERISTICS, which is a continuation of U.S. Ser. No. 025,345, filed Mar. 13, 1987 of the same title. This application combines the application of electronic sensing aperture principles, the specificity of selected biological molecules for identifying and/or enumerating defined populations of cells or formed bodies and microscopic particle technology. The automated analyzer can be used together with a special lysing reagent and/or antibodies coupled to microscopic microspheres or supports of varying composition.

A second application, U.S. Ser. No. 849,481, filed Mar. 10, 1992, now U.S. Pat. No. 5,231,005, which is a continuation of; U.S. Ser. No. 285,856, filed Dec. 16, 1988, entitled METHOD AND APPARATUS FOR SCREENING CELLS OR FORMED BODIES WITH POPULATIONS EXPRESSING SELECTED CHARACTERISTICS, discloses the screening of direct subsets from whole blood samples or portions thereof.

A third application, U.S. Ser. No. 339,156, filed Apr. 14, 1989, now U.S. Pat. No. 5,260,192, which is entitled METHOD AND APPARATUS FOR SCREENING CELLS OR FORMED BODIES WITH POPULATIONS EXPRESSING SELECTED CHARACTERISTICS UTILIZING AT LEAST ONE SENSING PARAMETER, discloses multipart or five part white blood cell differentials, lymphocyte subsets and overlapping determinations performed from a whole blood sample or from a sample with the red blood cells and/or populations of the white blood cells removed by elimination of populations and/or subsets thereof with one or more light or electronic parameters.

A fourth application, U.S. Ser. No. 07/525,231, filed May 17, 1990, entitled METHOD AND APPARATUS FOR SCREENING OBSCURED OR PARTIALLY OBSCURED CELLS, discloses an analysis of obscured cells by utilizing microspheres having specific monoclonal antibodies bound thereto to move the sensed characteristics of the obscured cells from one cell population area on a scattergram to another area. Each of the four above referenced applications is incorporated herein by reference.

An improved analytical hematology instrument and methods of utilizing the same are disclosed in U.S. Ser. No. 025,442 filed Mar. 13, 1987 (abandoned) and continuing U.S. Ser. No. 129,954 filed Dec. 4, 1987, now abandoned in favor of continuation-in-part application U.S. Ser. No. 479,199, filed Feb. 13, 1990, now U.S. Pat. No. 5,125,737; both entitled MULTI-PART DIFFERENTIAL ANALYZING APPARATUS UTILIZING LIGHT SCATTER TECHNIQUES and are incorporated herein by reference. This hematology instrument utilizes light scattering and electronic sensing techniques to obtain a multi-part differentiation of the leukocyte (L) WBC population. This hematology instrument, however, does not perform differentiation of L subsets, since such subsets are obscured in the L population.

Selectively attaching microscopic particles to each cell of a cell population makes possible the modification of the parameter(s) responsible for the original location of at least one of the populations. The addition of a plurality of microscopic particles to each cell of selected target populations where this addition affects the measured volume and/or opacity results in shifting the location of the dots in the scattergram representing a population.

Antibodies of known specificity are employed in coating microscopic particles. This coating gives the particle the capacity to selectively attach to certain cells which express the antigen the antibody is specific for. These coated or tagged cells are a combination of particles and a cell which behave like a new entity. Their parameters of opacity, volume, or both opacity and volume may be considered to represent the sum of the effects of both the cell and the particles on the signals obtained. If the characteristics of the components are different, the new entity will move to a new position on a scattergram in accordance with the net effect. The new location, in contrast with the former position of the cell alone, should allow a classification of such new entity or group of new entities. If the particles attached to the cells are magnetic, then, of course, according to current practice, the new entities can be captured by the use of a magnet. If mixed rapidly, unexpected results including complete capture of a population without adversely affecting the properties of the cells under study occur.

Only three distinct populations of cells can be readily identified and enumerated from a blood sample by utilizing their inherent and unique properties of DC volume and opacity parameters heretofore stated. Additional steps such as improved lysing systems, must be taken to enable the detection and enumeration of more populations. Of course, these additional populations represent subpopulations of the three basic ones referred to as lymphocytes, monocytes and granulocytes. The steps performed in accordance with the above referenced applications demonstrate how subpopulations of these basic three populations are obtained.

Employing such simple aperture sensing techniques in combination with two or more biological particles, one can produce a unique and new position of the dot cluster representing a given population. This selective movement of populations on the dot plot or scattergram is reproducible and can be used to classify a population separate from the basic three populations.

The original and inherent combination of DC volume and opacity sensing techniques can be modified through the attachment of microscopic particles to selected individual cells. The selectivity is given the particles by the nature or specificity of the biological molecules, antibodies among others, employed as the coating on the particle surfaces. A population of cells alone, having no particles on their surface, may occupy a dot plot position no different from other populations or subpopulations, and, henceforth, not be distinguishable from one another. The addition of particles having a selective attraction to a specific population of cells which one seeks to identify, enumerate, and study is possible using this approach. The selective addition of a sufficient mass of selective particles to a distinct population of interest results in the shifting of that population's dot plot location as a result of the new and unique combination of mass, volume and opacity of each cell.

The method and apparatus embodying the invention can be utilized with a variety of immunological reactions, such as immunological reactions involving reactants and formed bodies or cells. The invention also applies to analyses of formed body suspensions such as some bacteria and viruses among others. As utilized herein, cells are defined as animal or plant cells, including cellular bacteria, fungi, which are identifiable separately or in aggregates. Cells are the least structural aggregate of living matter capable of functioning as an independent unit. For example, cells can be human RBC and WBC populations, cancer or other abnormal cells from tissue or from blood samples. Formed bodies are defined as some bacteria and viruses. The cells and formed bodies suitably tagged or labeled, reasonably can be expected to be optically identified by the method and apparatus of the invention in the same manner as the human blood cell examples.

Although the term "reactant" has been utilized in the above applications to define lysing agents and monoclonal antibodies, reactants can include various agents which detect and react with one or more specific molecules which are on the surface of a cell or formed body. Some examples are given below:

| Reactant | : | Specific Molecule |
|---|---|---|
| Antibody | | Antigen |
| Drug | | Drug Receptor |
| Hormone | | Hormone Receptor |
| Growth Factor | | Growth Factor Receptor |

The reactants couple or bind to the specific molecule(s) on the cells. These reactants do form part of a chemical reaction; however, the reactants are not necessarily chemically altered.

SUMMARY OF THE INVENTION

The invention provides a method and apparatus for performing screening of one or more cell groups of interest obscured by a cell population such as one or more subsets of interest of a WBC population. The cell group of interest is enumerated by utilizing microspheres having monoclonal antibodies bound thereto to modify the sensed characteristics of specified cells to differentiate the cell group of interest from the obscuring cell population.

A whole blood sample or portion thereof can be screened to provide the desired analysis of a WBC subset of interest. The sample portion is mixed with microspheres having monoclonal antibodies specific to the WBC subset of interest, which microspheres bind to the cells of interest to shift the sensed characteristics of the cells. The sample portion with the WBC subset of interest then is sensed by at least two sensing parameters, one of which is a light sensing parameter and the characteristics of the WBC subset of interest are shifted sufficiently to directly measure the subset of interest. Overlapping cell populations also can be analyzed.

A sample portion also can be measured first, then have specified cells deleted therefrom to enable the cell group of interest to be sensed in an area in which it would otherwise have been obscured by the deleted cells. The sample portion is again measured and compared to the first measurement to differentiate the cell group of interest. In a whole blood sample the cell group of interest could be immature cells or WBC subset populations of interest otherwise obscured by a WBC cell population.

BRIEF DESCRIPTION OF THE DRAWINGS

FIGS. 4A–4C are scattergrams illustrating a conventional scattergram modified by the techniques of the present invention to obtain the WBC subset of interest;

DESCRIPTION OF THE PREFERRED EMBODIMENTS

Figure 1:
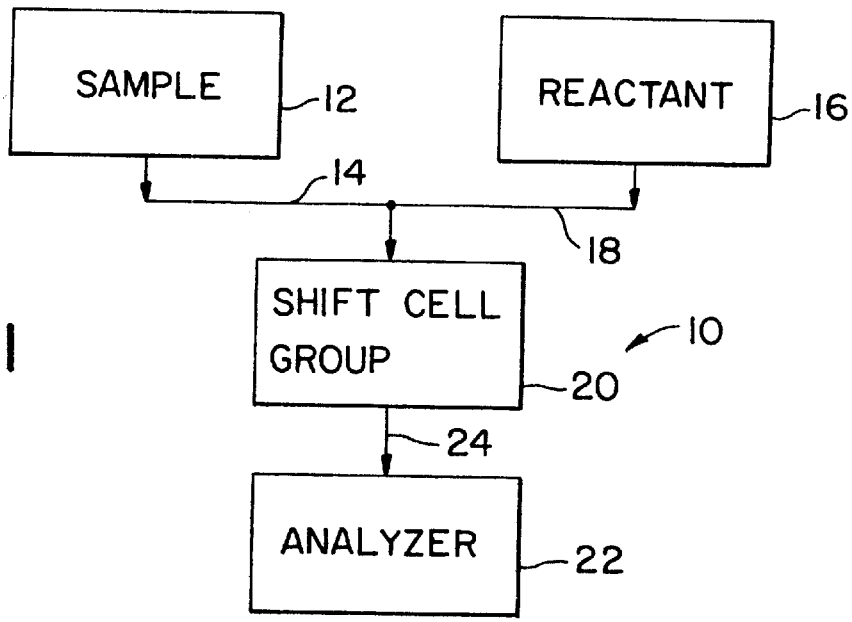
FIG. 1 is a schematic block diagram of one cell screening analyzer embodiment of the present invention.

Referring to FIG. 1, a first cell screening analyzer embodiment of the present invention is designated generally by the reference numeral 10. The analyzer 10 includes a sample 12, which contains at least a first set or population of cells (not illustrated). This cell population obscures a cell group of interest, such as a subset or second set of cells, when analyzed as described hereinafter. The sample 12 can include a buffer into which the cells are added.

The sample 12 or a portion thereof is combined via a line 14 with at least one reactant 16 via a line 18. The cells of the cell group of interest have at least one sensed cell characteristic modified or shifted in a shift cell group station 20. The sensed characteristic of the cells of the cell group of interest is modified or shifted sufficiently to remove the cell characteristics from the sensed cell characteristics of the obscuring cell population.

The reactant 16 can be or can include a plurality of microspheres with an antibody bound thereto which is specific to the cell group of interest. The reactant 16 and the sample portion 12 preferably are mixed together to enhance the binding of the microspheres to the cell group of interest. A plurality of the microspheres are bound to each cell of the cell group of interest, generally coating each cell with microspheres, which modifies or shifts the resultant sensed characteristics of each cell of the cell group of interest. The sample portion 12 then is fed into an analyzer 22 via a line 24. The analyzer at least senses and counts the number of cells in the sample portion 12. The analyzer 22 includes at least two sensing parameters, at least one of which is an optical parameter, as will be further described hereinafter.

Figure 2:
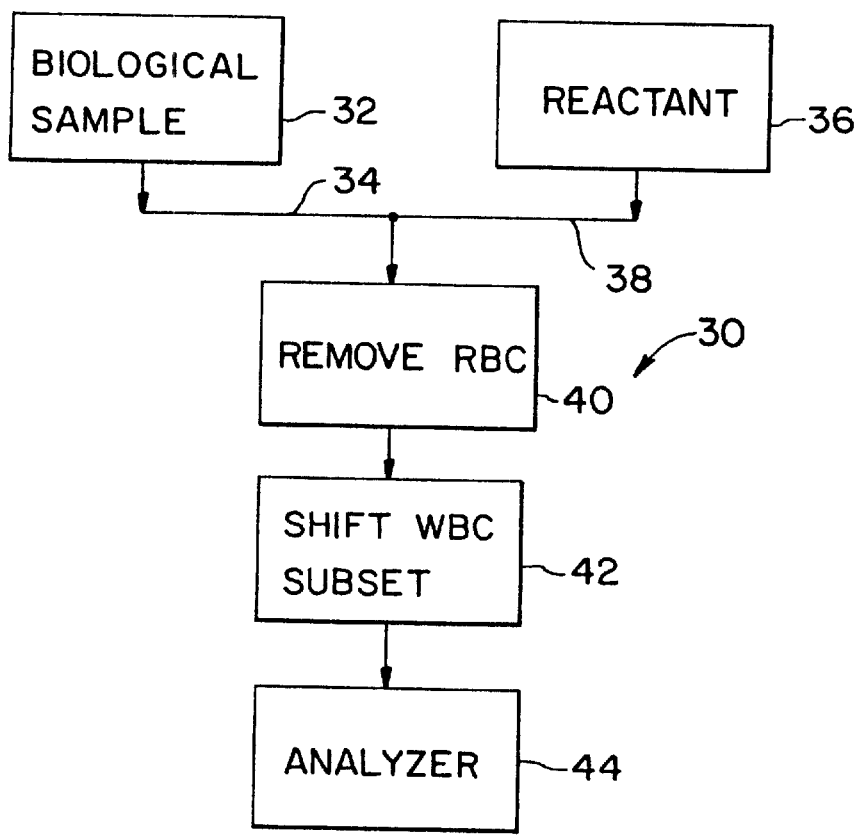
FIG. 2 is a schematic block diagram of a second cell screening analyzer embodiment of the present invention.

Referring to FIG. 2, a second cell screening analyzer embodiment of the present invention is designated generally by the reference numeral 30. The analyzer 30 includes a biological sample 32 which contains at least a first set of viable biological cells (not illustrated), such as in or from a whole blood sample. The cells of the biological sample 32 are to be involved in a biological reaction in a quantitative and/or qualitative determination or analysis. The biological sample 32 includes at least one WBC population, which WBC population obscures a WBC subset population of interest. The sample 32 can also include a buffer into which the cells are added.

As utilized herein, WBC subset populations are subsets of a WBC population to which specific monoclonal antibodies can be bound. A nomenclature now has been defined for the monoclonal antibodies by the World Health organization and the International Immunology Society. The monoclonal antibodies are defined by a cluster designation (CD) nomenclature which defines a particular specificity for a cell or group of cells and the monoclonal antibodies specific for that CD group. For example purposes only, three CD groups have been utilized in the following examples, CD2, CD4 and CD8. The CD nomenclature, specificity and some commercial sources of monoclonal antibodies are illustrated in Table I.

TABLE I

| Cluster of Differentiation | Antibody (Commercial Source)[b] | Specificity |
|---|---|---|
| CD2(gp 50)[a] | T11 (Coulter) OKT11 (Ortho);Leu5a (BD) | E Rossette Receptor |
| CD4(gp 56) | T4 (Coulter) OKT4$_a$ (ortho);Leu3a (BD) | Helper/inducer T |
| CD8(gp 32–33) | T8 (Coulter) OKT8 (Ortho);Leu2a (BD) | Cytotoxic/ Suppressor T |

[a]gp - glycoprotein, molecular weight in kilodaltons
[b]Coulter - Coulter Immunology Division of Coulter Corporation (Hialeah, fflorida)
BD - Becton-Dickinson Immunocytometry Systems
Ortho - Ortho Diagnostic Systems (Raritan, New Jersey)

The sample 32 or a portion thereof is combined via a line 34 with at least one reactant 36 via a line 38. The red blood cells (RBC) then are removed from the mixture by a functionally designated RBC removing station 40. The RBC's can be removed from the mixture by the station 40 in a number of ways. The RBC's can be lysed by a lyse in the reactant 36. One such preferential lyse and a quench which can be utilized therewith is disclosed in Ser. No. 130,911, filed Dec. 10, 1987, now abandoned favor of continuation application U.S. Ser. No. 611, 378, filed Nov. 13, 1990, entitled METHOD AND REAGENT SYSTEM FOR ISOLATION, IDENTIFICATION AND/OR ANALYSIS OF LEUKOCYTES FROM WHOLE BLOOD SAMPLES, which is a CIP of Ser. No. 025,303, filed Mar. 13, 1987, now abandoned in favor of continuation application U.S. Ser. No. 317,147, filed Feb. 28, 1989, and of the same title, which are incorporated herein by reference. The reactant 36 can be or can include a plurality of magnetic microspheres with an antibody specific to the RBC's bound to the microspheres (not illustrated). In this example, the particular red blood cell specific antibody utilized is disclosed in U.S. Pat. No. 4,752,563, entitled MONOCLONAL ANTIBODY FOR RECOVERY OF LEUKOCYTES IN HUMAN PERIPHERAL BLOOD AND METHOD OF RECOVERY EMPLOYING SAID MONOCLONAL ANTIBODY, which is incorporated herein by reference. The reactant 16 also can include a buffer in addition to or in place of the sample buffer. The reactant 36 further can be a combination of the preferential RBC lyse and the RBC specific microspheres.

Once the RBC's substantially are removed from the sample portion mixture 32, a portion of the mixture is fed into a subset shift station 42. As in the analyzer 10, the WBC subset population of interest will have at least one sensed cell characteristic modified or shifted in the station 42 to remove the sensed characteristics of the WBC subset population of interest from the sensed cell characteristics of the obscuring WBC population.

Again, the reactant 36 can be or can include a plurality of microspheres with an antibody bound thereto which is specific to the WBC subset population of interest. The reactant 36 and the sample portion 32 preferably are mixed together to enhance the binding of the microspheres to the WBC subset population of interest. A plurality of the microspheres are bound to each cell of the WBC subset population of interest, coating each cell with microspheres, which modifies or shifts the resultant sensed cell characteristic of each cell of the WBC subset population of interest.

The magnetic microspheres utilized can be of any suitable type and for example, are polystyrene magnetic microspheres of 0.7 micron diameter, with a weight to volume of 10% solids, sold by Bangs Laboratories of Carmel, Ind. The non-magnetic microspheres again can be of any suitable type and for example, are surfactant free sulfated polystyrene latex microspheres of 2.17 micron diameter with a weight to volume of 8% solids, sold as IDC microspheres by Interfacial Dynamics of Portland, Oreg. Although these specific microspheres are utilized for example purposes, other types and sizes of microspheres from other conventional sources also can be utilized.

In general, for shifting, it is preferable to utilize microspheres of a diameter substantially less than the diameter of the cells, since a plurality of the microspheres should bind to each cell. Typically, microspheres of diameters from 0.65 to 3.0 microns are utilized to ensure that the instrument does not sense and count the free microspheres themselves as an indicated cell. Further, very large microspheres could clog or block the sensing apertures, since a plurality of cells could be bound thereto, resulting in a large microsphere and cell mass. Typically, non-magnetic microspheres are less expensive and hence are utilized for shifting purposes, although magnetic microspheres also can be utilized to cause the sensed cell shift.

To eliminate cells magnetically, only magnetic microspheres can be utilized. In this application, the microsphere size is less relevant, since the cells are to be eliminated from the sample before sensing. The microspheres should be of sufficient means to quickly and easily be removed in the magnetic field. In this case, 0.65 to 4.5 micron diameter microspheres work well. Further, since the cells only are to be eliminated, 10 or greater micron diameter microspheres could be utilized. A plurality of cells could be bound to each microsphere, but since no counting will take place, this does not interfere with the operation of the instrument.

The sample portion 32 then is fed into an analyzer 44 which can be identical to the analyzer 22, again at least sensing and counting the number of cells in the sample portion 32.

Figure 3:
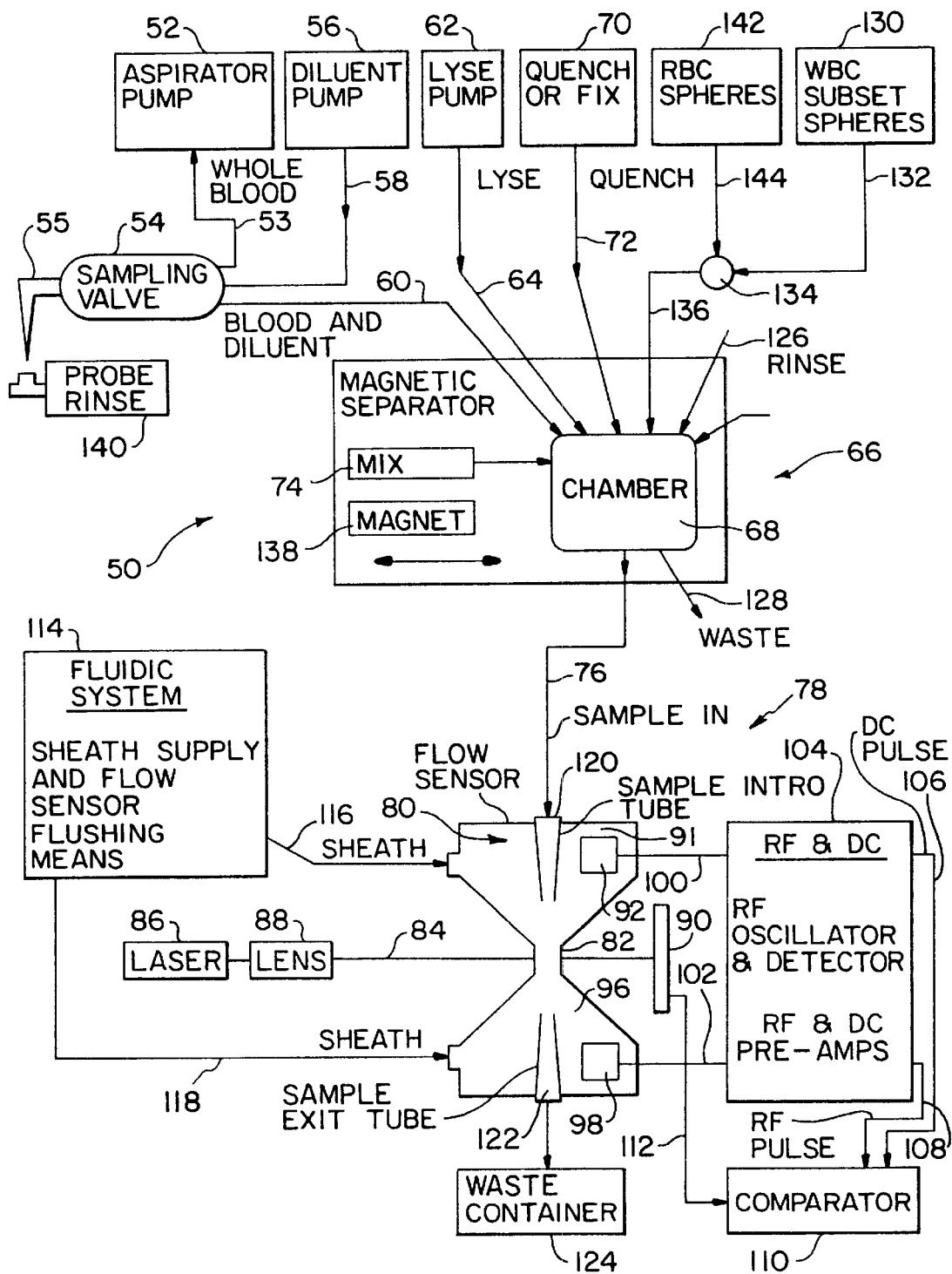
FIG. 3 is one specific analyzer embodiment of the present invention.

One specific embodiment of an analyzer instrument embodying the present invention and which can accomplish the analyzing methods of the first and second analyzers 10 and 30, is designated generally by the reference numeral 50 in FIG. 3.

In the instrument 50, only one specific enumeration is illustrated, which can be varied in almost endless detail in accordance with the principles of the present invention. Further, the instrument 50 is shown in generally functional detail and the specific embodiments can be structurally implemented in many known ways.

The instrument 50 includes an aspirator pumping mechanism 52 which is utilized to draw the cell sample of interest, for example the sample 12 or 32 into the instrument 50. The aspirator 52 is coupled via a line 53 to a sampling valve 54, which can be coupled to a sample probe 55. A diluent pump 56 can include a diluent or buffer solution and also is coupled to the valve 54 via a line 58. The valve 54 and the pump 52 can aspirate the cell sample 12 or 32 along with the diluent via the pump 56 when appropriate.

The reactant mixture or the cell sample itself, then is fed via a discharge line 60 into a mixing apparatus 66. The mixer 66 includes a mixing chamber 68 into which the sample or reactant is fed. The RBC's then will be lysed by a lyse from a lyse pump 62 fed into the chamber 68 via a line 64. When the reaction is completed a quench or fix then is supplied from a station 70 via a line 72. The reaction can be assisted by mixing the lyse and/or the quench and the sample in the chamber 68 as illustrated functionally at 74.

Specific details of an appropriate mixing apparatus 66, which can be utilized herein are disclosed in Ser. No. 025,337, filed Mar. 13, 1987, and Ser. No. 517,309, filed May 1, 1990, now U.S. Pat. No. 5,238,812, which is a continuation of Ser. No. 025,337 both entitled METHOD AND APPARATUS FOR RAPID MIXING OF SMALL VOLUMES FOR ENHANCING BIOLOGICAL REACTIONS, which are incorporated herein by reference. By utilizing the mixer 66 the reactions are greatly enhanced in speed without significantly damaging the properties of interest of the cells, such as, can occur by raising the reaction temperature. Further, the reactions generally are completed in a significantly reduced time, generally on the order of two minutes or less. This allows a rapid analysis for the automatic high volume analyzer instrument 50.

The quenched sample portion with the RBC's removed by the lyse can be fed via a line 76 directly to a WBC analyzer 78 (i.e., analyzer 22 or 44 ). The sample portion is fed directly to the analyzer 78 where a reference or non-shifted result is first obtained from the sample for later reference or comparison purposes. The analyzer 78 can be of many physical types in accordance with the counting and sizing techniques described by Wallace H. Coulter in U.S. Pat. No. 2,656,508 and embodied in the numerous commercial blood cell counters of the assignee, Coulter Electronics, Inc.

The analyzer 78, in general, includes a flow cell type of sensing chamber 80. The flow cell 80 includes at least optical and preferably electronic sensing devices. The flow cell 80 is formed from any optically transparent material, for example fused silica or quartz. The flow cell 80 includes a narrowed necked-down aperture 82 through which the sample portion flows as a hydrodynamically formed stream in a well known manner. The flow cell 80 includes an optical flat surface for focusing a beam 84 of electromagnetic light energy, preferably from a laser source 86 focused through a lens arrangement 88 into a spot in the aperture 82. The light scattered by the individual cells as they pass through the aperture 82 and hence the beam 84 is detected by a detector arrangement 90, again in a well known manner. One system hereinafter VCS system, which discloses a light sensing system which can be utilized herein is described in U.S. application Ser. Nos. 025,442 and 129,954, above referenced, which are incorporated herein by reference.

The flow cell 80 also includes electronic sensing circuitry. The flow cell 80 includes a first portion 91 having a first electrode 92 in contact with the fluid therein.

The flow cell chamber portion 91 and the electrode 92 communicate through the aperture 82 with a second chamber portion 96 having a second electrode 98 therein. The electrodes 92 and 98 are coupled via reactive leads 100 and 102 to an RF/DC source and sensing circuit 104. The circuit 104 couples both a DC, or low frequency current or signal, and a high frequency signal between the electrodes 92 and 98.

The low frequency signal is utilized to sense the amplitude of a signal pulse caused by a cell passing through the aperture 82. The high frequency signal is utilized to obtain the electrical opacity of the same cell passing through the aperture 82.

The measuring of the electrical opacity of cells was described by Wallace H. Coulter and Walter R. Hogg in U.S. Pat. No. 3,502,974 and several patents and publications of the assignee, Coulter Electronics, Inc., since that patent. One specific circuit which can be utilized herein is disclosed in U.S. Pat. No. 4,791,355, entitled PARTICLE ANALYZER FOR MEASURING THE RESISTANCE AND REACTANCE OF A PARTICLE, which is incorporated herein by reference.

The signals generated by the circuit 104 from the sensed cells are coupled via a DC signal lead 106 and an RF signal lead 108 to a comparator 110. The comparator 110 can hold the signal generated from the sample portions, i.e., for a comparison with the results from the other sample portions to be described. Also, the comparator 110 can include an optical sensing input or inputs via a lead 112 from the optical detector arrangement 90.

The analyzer 78 includes a sheath flow to focus the cells in the flow cell 80, in the well known manner. The sheath flow can be provided by a fluidic system 114, coupled to the flow cell 80 by a pair of lines 116 and 118 in a known manner. The sample reaction mixture can be fed into the flow cell 80 via an introduction tube 120 and can be fed from the flow cell 80 via an exit tube 122 into a waste container 124.

While the first portion of the mixture was being analyzed in the analyzer 78, the mixer 66 can be cleaned or flushed via a rinse line 126 and exhausted through a waste line 128. A second sample portion now can be fed into the chamber 68 to have its sensed cell characteristics modified or shifted. Alternatively, the sample portion to be modified can first be fed into the chamber 68, without a first non-shifted or standard sample portion result first being obtained. The WBC or other cell group of interest now is shifted by adding the WBC microspheres from a station 130 via a line 132, a valve 134 and a chamber line 136 into the chamber 68 to be mixed with the sample portion.

The WBC microspheres are mixed with the second portion by the mixing mechanism 74. For shifting, the WBC microspheres and the reaction mixture with the bound WBC microspheres is fed via the line 76 into the analyzer 78 (i.e., the analyzer 22 or 44 ), wherein the second portion is analyzed like the first portion and the results then can be compared in the comparator 110. At least one of the WBC subset sensed cell characteristics is changed in the second portion, such as the cell opacity by the WBC subset bound microspheres to provide the changed results which then can be analyzed.

If the WBC microspheres are magnetic, for reasons described hereinafter, then the WBC subset population bound thereto can be removed by a magnetic field during and/or after the mixing process by a magnetic field or magnet 138. The field can be provided by electromagnetic means or by the magnet 138 being physically moved with respect to the chamber 68 to capture the magnetically bound WBC subset. The second portion without the bound WBC subset then is fed via the line 76 to the analyzer 78 in the manner previously described to obtain the analysis.

The instrument 50 then is prepared to take the next sample or sample portion for the next analysis. The probe 55 can be cleaned by a probe rinse mechanism 140 and the lines and chamber 68 can be flushed in a conventional manner. Each analysis of the succeeding sample mixture is obtained in a rapid and automatic fashion. The period between the analysis of succeeding sample mixtures can be on the order of minutes or less.

In operating the analyzer instrument 50, the sample portion preferably first is mixed in the chamber 68 along with non-magnetic WBC microspheres from the station 130, which bind to one of the WBC subsets. The RBC lyse then is added to the mixture. The quench 70 is added to the reactive mixture which then is fed via the line 76 to the WBC analyzer 78 for analysis.

Alternatively to the utilization of the lyse, the sample 12 or 32 can be fed to the mixer 66 and the RBC's can be removed without lyse. In this case, the RBC's can be removed magnetically by utilizing the microspheres with the RBC specific antibody bound thereto from an RBC microsphere station 142 and fed to the valve 134 via a line 144 and hence to the chamber 68 via the line 136. Where lyse is not utilized, the bound RBC's are magnetically removed by the magnet 140 after mixing in a manner substantially identical to the magnetically bound WBC's described above.

Further, in a second case to promote the speed of the reaction, a reaction mixture of the sample with both the RBC lyse and with the RBC magnetic beads can be utilized. The reaction mixture is mixed, the lyse is quenched and the bound RBC's are magnetically removed and then the WBC's are analyzed as previously described.

Although the technique of the present invention has been described utilizing a sample in its natural state, such as a whole blood sample fed directly into the instrument 66, the sample also can be off line prepared or partially pre-prepared where desired. The sample could have the RBC's previously deleted. A, system such as the VCS system previously described, can be utilized in which case the microspheres could be added of f line or in a preparation mode and the sample portion with the sensed cell characteristics already shifted then could be introduced into the system for the rest of the analysis. Some specific examples, including utilizing a VCS system are described hereinafter.

Figure 4A:
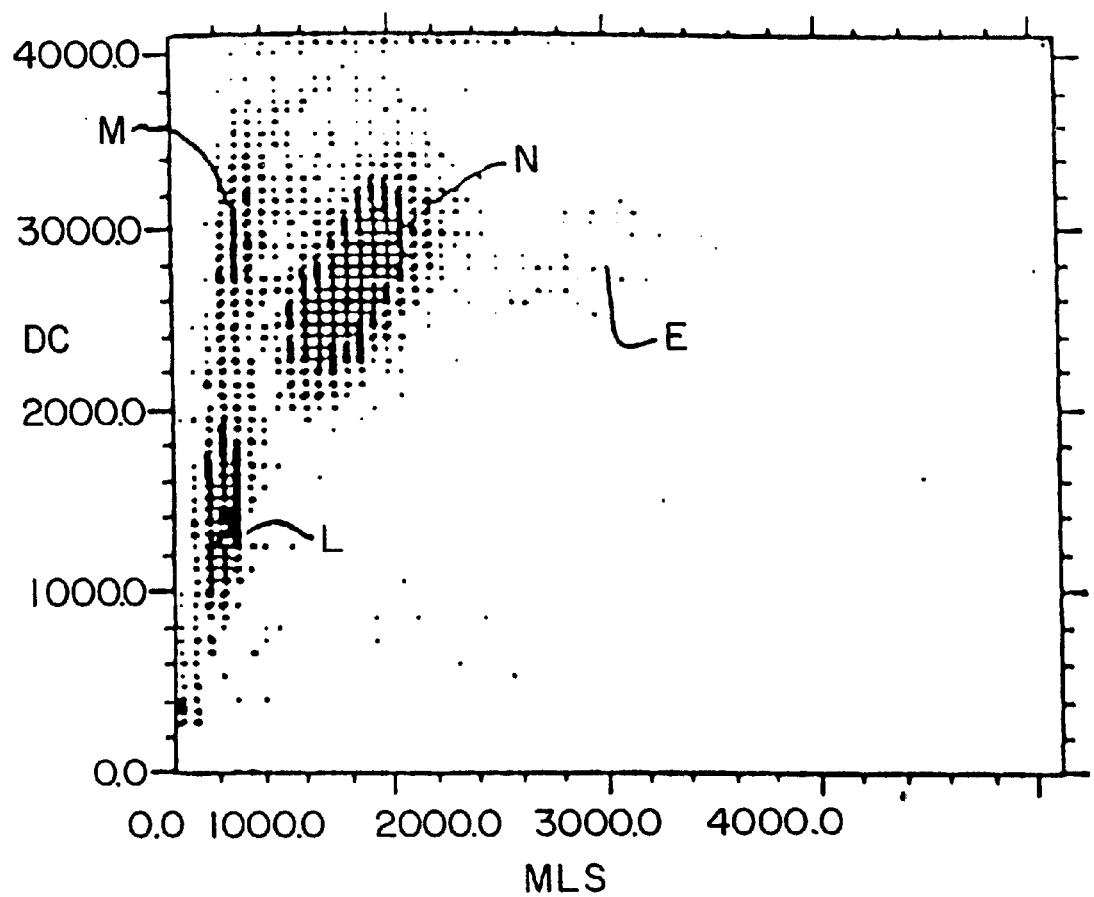

Referring to FIGS. 4A–4C, a standard VCS scattergram with the gain properly set provides, on a DC/median light scatter (MLS) plot as shown in FIG. 4A, four WBC population groupings monocytes (M's), L's neutrophils (N's) and eosinophils (E's), with no microspheres present. The scattergram depicts the results from a representative normal whole blood sample. The basophils (B's) are obscured by the L's in the scattergram. Although the B's partially obscure the L area, their percentage number of the WBC populations is of a small enough order to not substantially affect the desired calculations. However, the B's contribution can be subtracted from a calculation if so desired.

When microspheres are added, the light scattered by the microspheres blends the sensed characteristics such that only two WBC populations are separately enumerated as shown in FIG. 4B, 146 L's and 148 M's, N's, E's combined. By lowering the MLS gain (x axis), the patterns or populations 146 and 148 are shifted toward the DC or y axis, freeing the scattergram area further to the right of the DC axis to be utilized.

Utilizing FIG. 4B as the standard or control, then non-magnetic microspheres with a monoclonal antibody bound thereto specific to an L subset, such as T4, are mixed in the same sample or in a second portion of the sample resulting in a shift forming a direct subset grouping 150 in the now free area as shown in FIG. 4C.

Although the data in FIGS. 4A–4C has been depicted utilizing MLS as the light scatter parameter, light scatter information obtained at any angle can be utilized. For purposes herein and as defined in the above-referenced vcs patent application, MLS is defined as that light scatter information obtained at angles between 10 degrees and 70 degrees. RLS, rotated light scatter, is defined as a function whereby the pulse peak information derived from the logarithm of MALS, plus a constant, is divided by DC, as before defined, plus a constant. This RLS function has the effect of removing a size component, yielding a measurement which is more related to internal structure. An alternative method for obtaining RLS consists of dividing the logarithm of MALS signal data by the logarithm of the DC signal data. Light scatter information defined as centered at 90 degrees to the laser axis is called 90 degrees or HALS (high angle light scatter). Light scatter information defined as obtained around 0 degrees relative to the laser axis in the forward direction is called FWD. The data in the scattergrams is depicted utilizing different parameters to provide the best representation of the data of interest.

This procedure can be utilized off-line or on-line. Utilizing a conventional VCS instrument, steps 1–3 of the procedure would be accomplished off-line, since the VCS instrument currently does not include the equipment necessary to add the microspheres and mix them with the sample. A fully automatic instrument 50 could accomplish all the steps automatically on-line. The off-line procedure, in general, is as follows:

1. Provide 150 microliters of whole blood (or more).
2. Add 15 microliters of non-magnetic 2 micron microspheres having one L subset specific monoclonal antibody bound thereto (T4, T8 or T11 each in a separate mixing vessel) or add 15 microliters of MSIG control microspheres to form a control or background standard. (MSIG is a mouse monoclonal immunoglobin having no specificity for any WBC or WBC subset population).
3. Mix 2 minutes (can stand for a period of time afterwards, at least up to an hour).
4. Introduce into (automatic) VCS system.
5. Lyse, quench, and analysis on-line in VCS system.

FIGS. 5A–5D, 6A–6D and 7A–7D are scattergrams of actual results on a VCS system instrument according to the techniques of the invention in accordance with FIGS. 4A–4C. FIG. 4A is a normal plot without microspheres with a normal gain setting. FIG. 4B is a plot with microspheres with the x-axis gain reduced to provide the two cell groupings and free area for the shifted cell group of interest. This modification of the conventional VCS x-axis sensing parameter moves the x scale of the cell groupings, to leave room on the scattergram for the sensed characteristics of the modified WBC subset of interest. Although, the actual data was derived utilizing a VCS system, the present invention encompasses any system as described with the gain set to produce the configuration of FIG. 4B, which then would be the standard system. Alternately, a system in accordance with the present invention can be capable of producing either of the sensing configurations embodied in FIG. 4A or FIG. 4B.

Figure 5A:
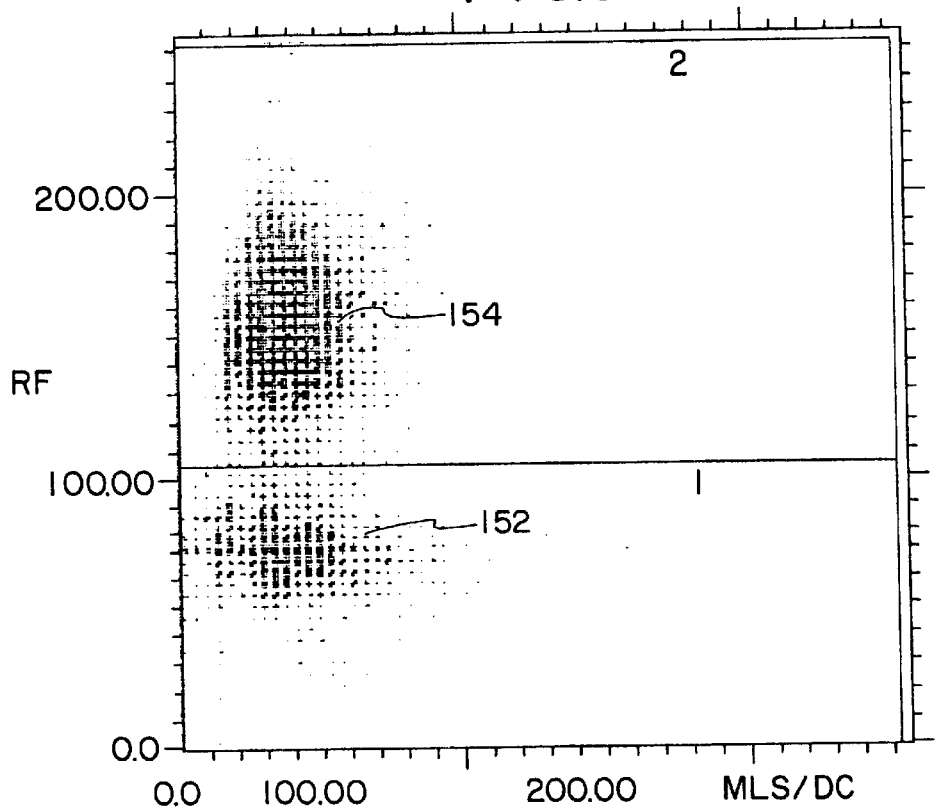
FIGS. 5A–7D are scattergrams of results for different WBC subsets of interest utilizing one of the techniques of the present invention.
Figure 5B:
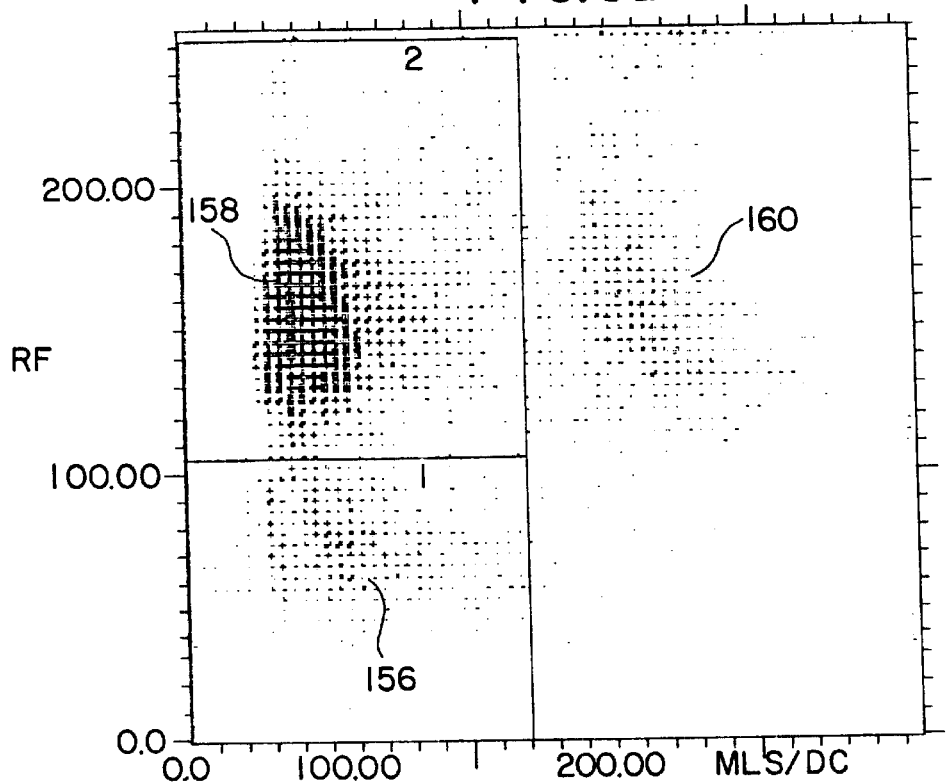
Figure 5C:
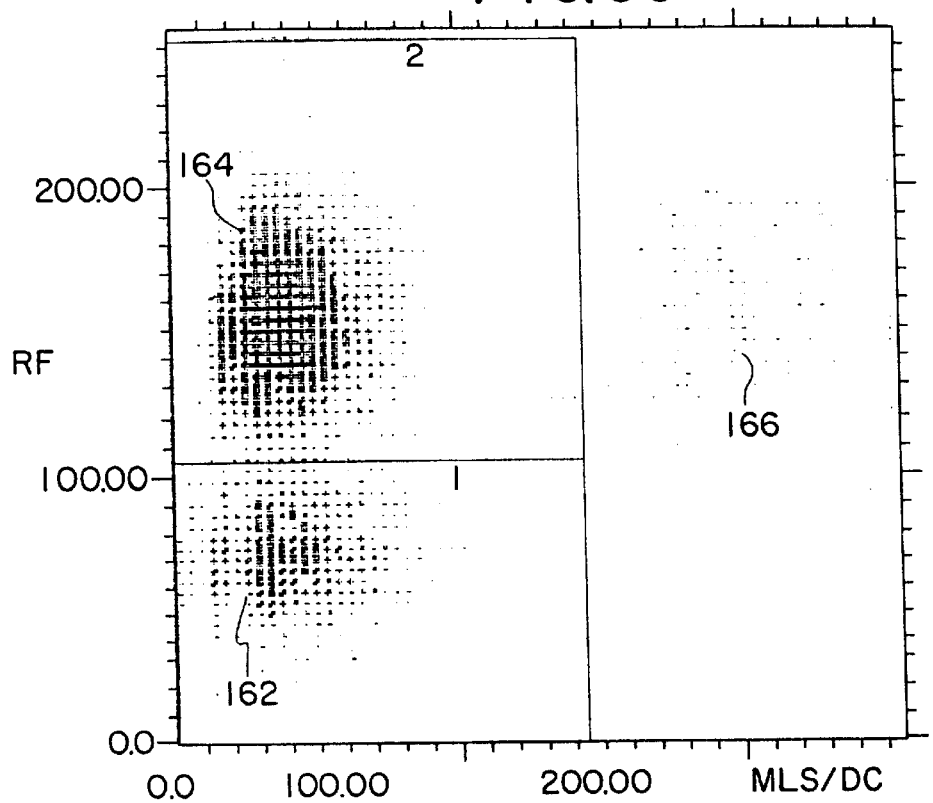
Figure 5D:
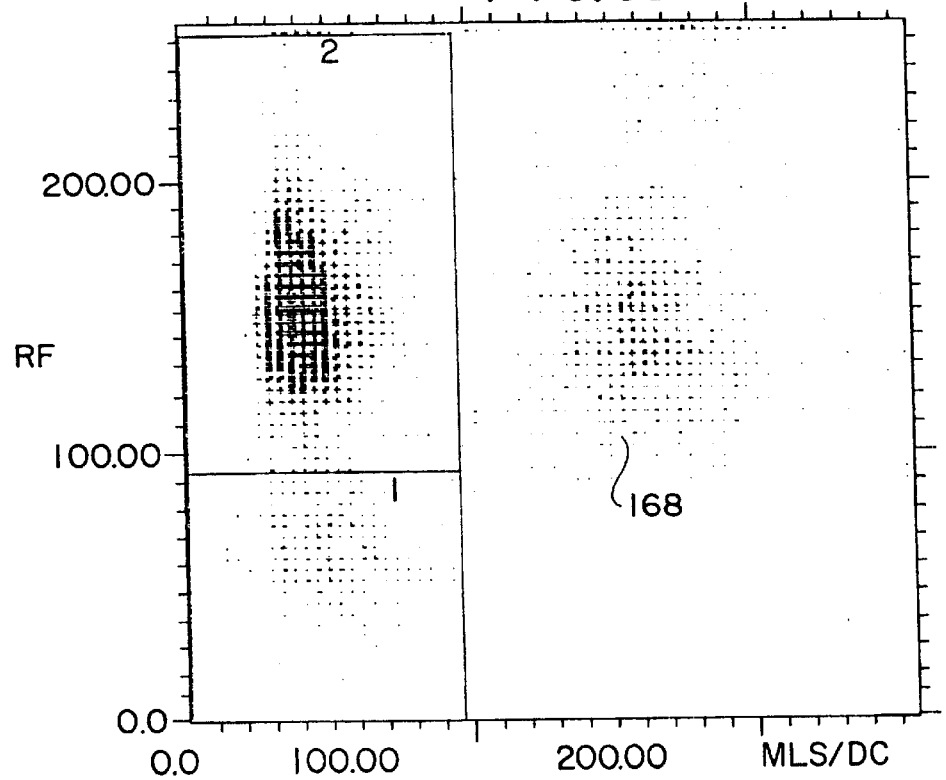

Referring to FIG. 5A, a control or non-shifted scattergram result is illustrated when utilizing non-binding control microspheres. The L's are found in a grouping 152, while the M's, N's and E's are found in a grouping 154. As stated above, the control need not be provided, since as can be seen in FIGS. 5B–5D, the WBC subset of interest can be located directly and therefor there is no need to compare back to a reference result. The MSIG control microspheres only are utilized to ensure that the scattergram pattern is free of interference.

A first WBC subset of interest, the CD4 cells are shifted by binding T4 microspheres thereto as illustrated in FIG. 5B. The L's without the shifted subset are shown in a grouping 156, while the M's, N's and E's are found in a group 158. The shifted sensed cell characteristic of the CD4 cells, form a new grouping 160, which can be compared to the results of FIG. 5A or can be analyzed directly as a percentage of CD4 cells to the total L's. In this example, the percentage contribution of the CD4 cells was found to be 59.6 percent. The same sample was analyzed in a conventional EPICS (registered trademark) flow cytometry instrument, for comparison purposes, which resulted in a percentage contribution of 60.6 percent.

In a like manner, the CD8 cells were analyzed as illustrated in FIG. 5C. The CD8 cells are shifted by binding T8 microspheres thereto. The L's are shown in a grouping 162, while the M's, N's and E's are found in a grouping 164. The shifted sensed cell characteristic of the CD8 cells form a separate grouping 166, which again provides the percentage contribution of the CD8 cells. The CD8 percentage contribution was found to be 14.4 percent. The flow cytometry comparison resulted in a percentage contribution of 14.0 percent.

The analysis of the CD2 cells is illustrated in FIG. 5D. The CD2 cells are shifted by binding T11 microspheres thereto resulting in the separate CD2 grouping 168. The CD2 percentage contribution was found to be 81.9 percent, while the flow cytometry comparison resulted in a percentage contribution of 77.2 percent.

The results of another analyzed sample are illustrated in FIGS. 6A–6D. FIG. 6A again is a non-shifted control scattergram, showing an L grouping 170 and an M, N and E grouping 172.

Figure 6A:
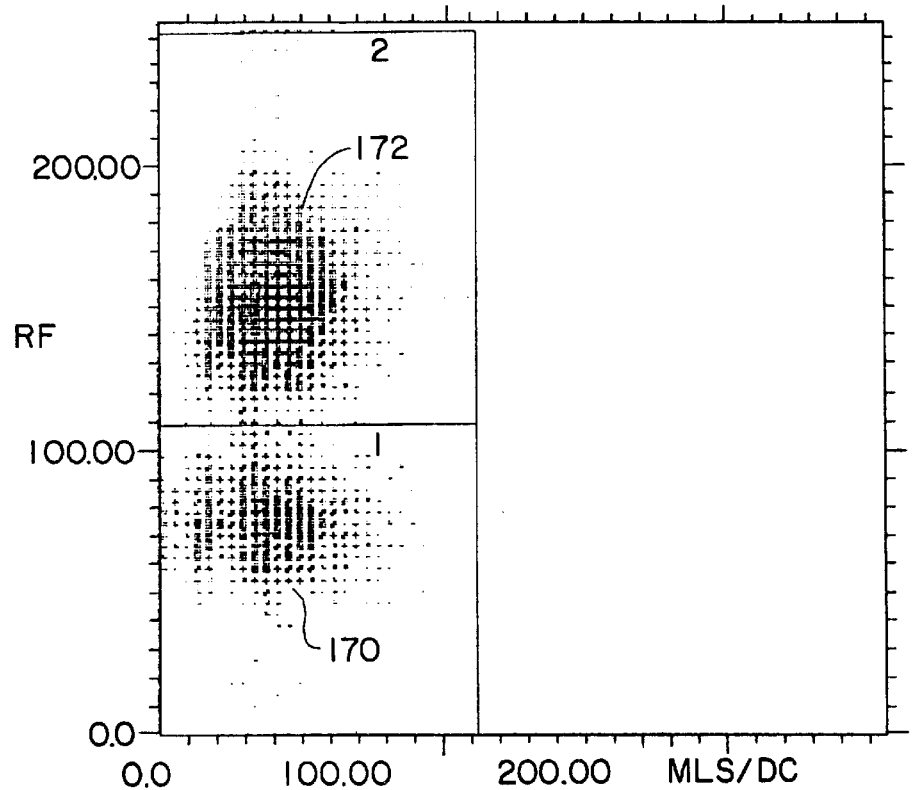
Figure 6B:
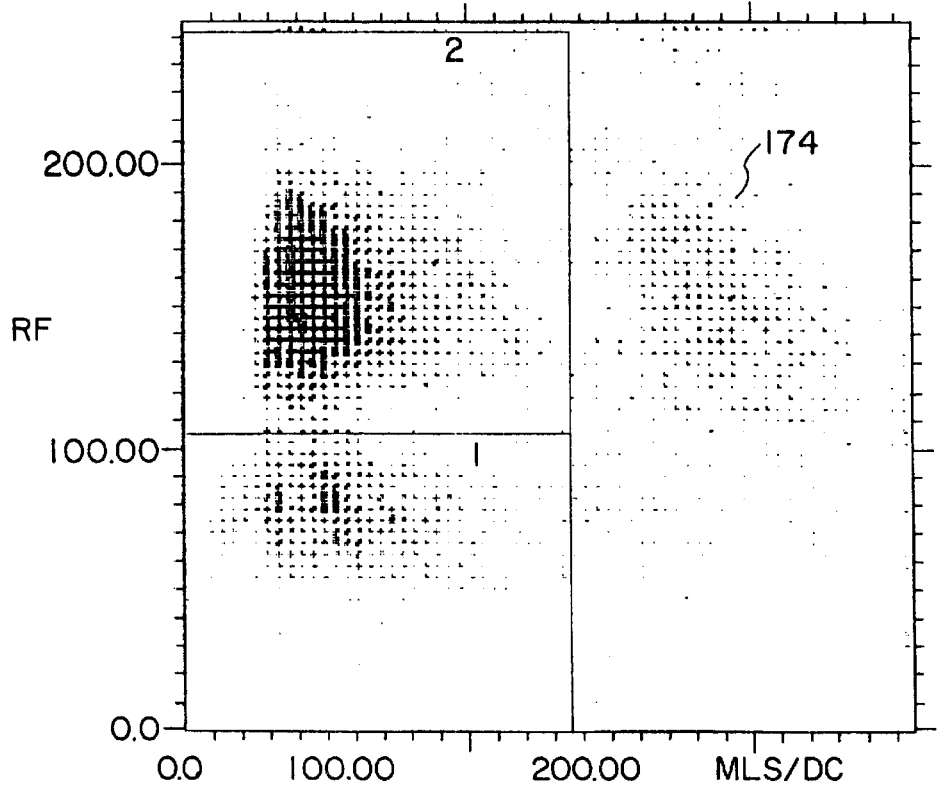

The CD4 shift results are illustrated by a grouping 174 in FIG. 6B. The CD4 percentage contribution was found to be 46.3 percent, while the flow cytometry comparison resulted in a percentage contribution of 46.9 percent.

Figure 6C:
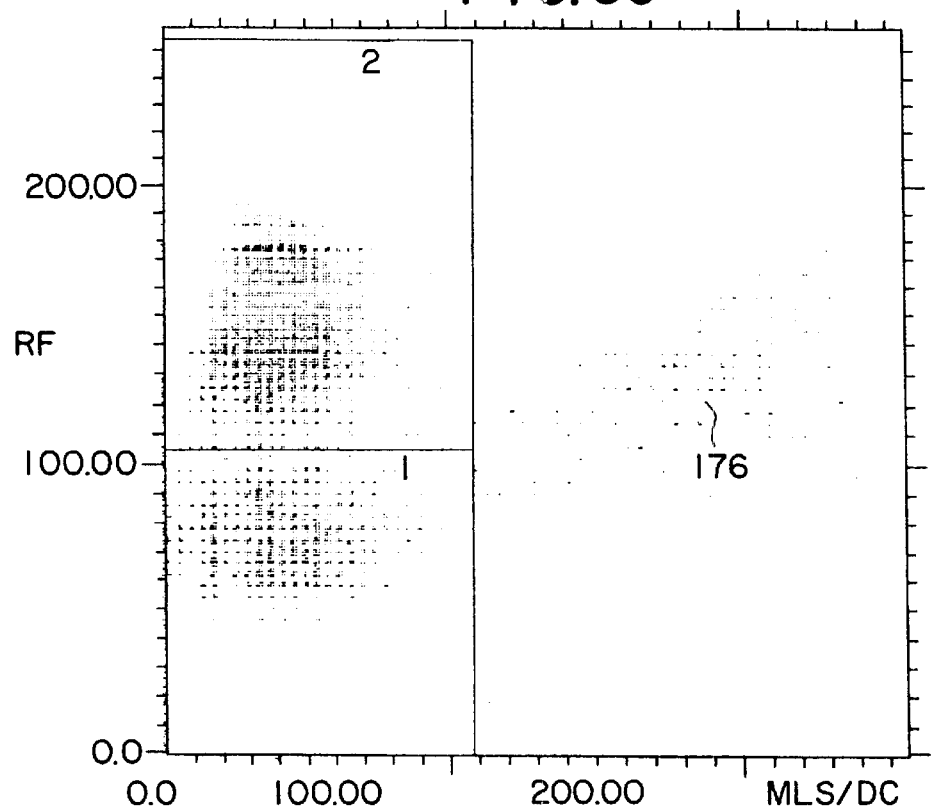

The CD8 shift results are illustrated by a grouping 176 in FIG. 6C. The CD8 percentage contribution was found to be 24.5 percent, while the flow cytometry comparison resulted in a percentage contribution of 20.8 percent.

Figure 6D:
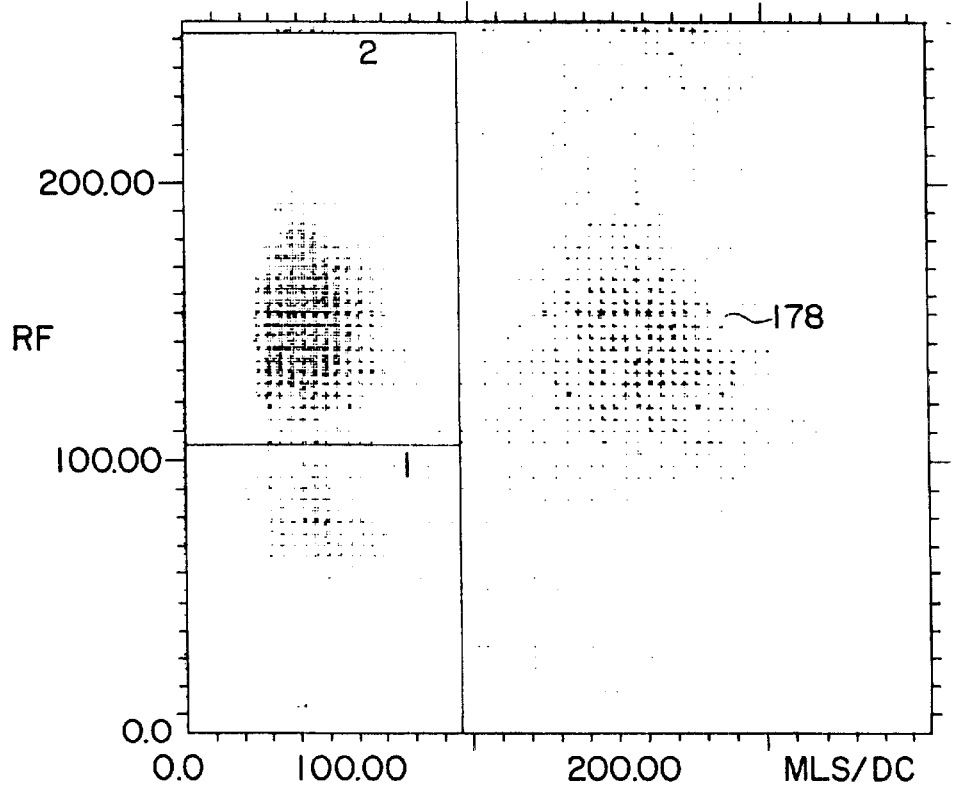

The CD2 shift results are illustrated by a grouping 178 in FIG. 6D. The CD2 percentage contribution was found to be 71.8 percent.

The results of a third sample analysis are illustrated in FIGS. 7A–7D. FIG. 7A again is a non-shifted control scattergram showing a L grouping 180 and an M, N and E grouping 182.

Figure 7A:
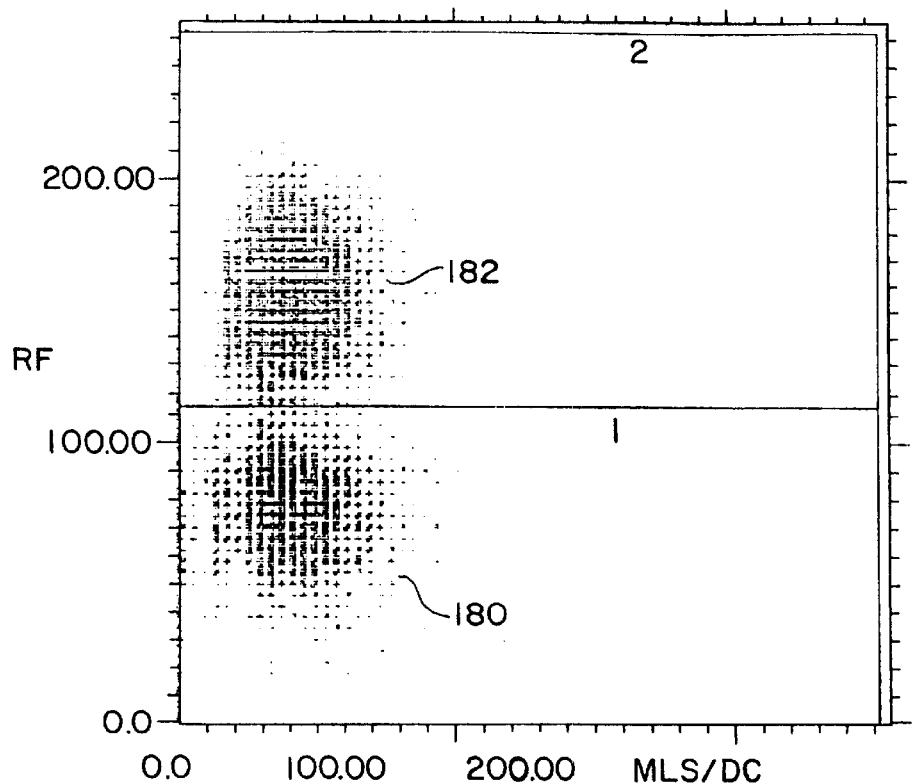
Figure 7B:
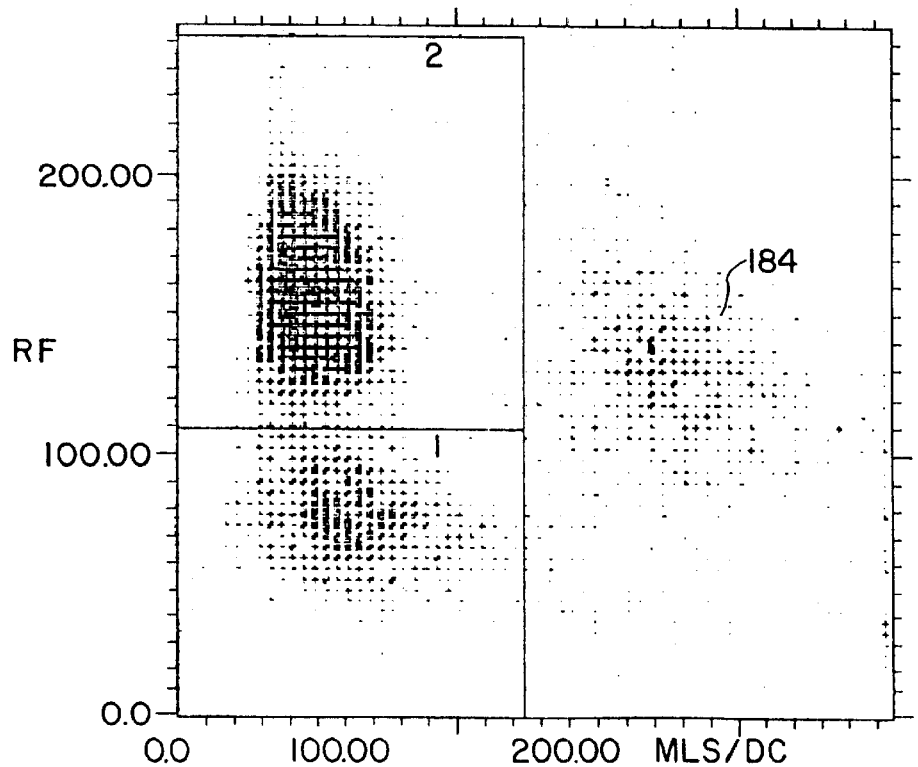

The CD4 shift results are illustrated by a grouping 184 in FIG. 7B. The CD4 percentage contribution was found to be 40.3 percent, while the flow cytometry comparison resulted in a percentage contribution of 38.1 percent.

The CD8 shift results are illustrated by a grouping 186 in FIG. 7C. The CD8 percentage contribution was found to be 33.6 percent, while the flow cytometry comparison resulted in a percentage contribution of 32.1 percent.

The CD2 shift results are illustrated by a grouping 188 in FIG. 7D. The CD2 percentage contribution was found to be 79.7 percent, while the flow cytometry comparison resulted in a percentage contribution of 75.4 percent.

Figure 8:
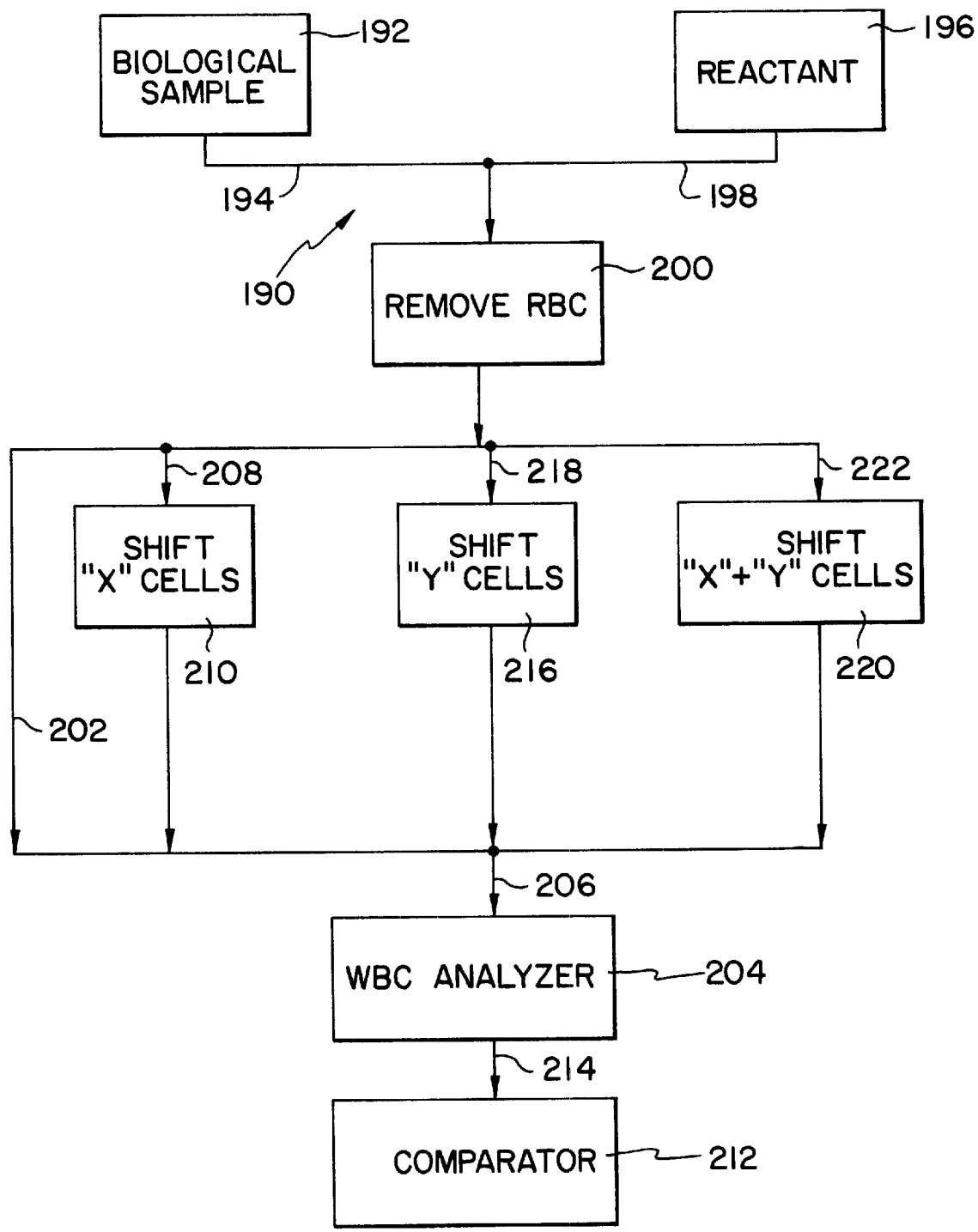
FIG. 8 is another schematic block diagram of one cell screening analyzer embodiment of the present invention for determining overlapping subsets.

Referring to FIG. 8, a third cell screening analyzer embodiment of the present invention is designated generally by the reference numeral 190. The analyzer 190 is utilized to determine the percentage overlapping of the cell groups of interest and will be described with respect to WBC population subsets of interest from a whole blood sample or portion thereof.

The analyzer 190 includes a biological sample 192, which again contains at least a first WBC population, including at least two WBC population subsets of interest. The biological sample 192 or a portion thereof is combined via a line 194 with at least one reactant 196 via a line 198. The RBC's then are removed from the sample portion by a functionally designated RBC removing station 200. The RBC's are removed by one of the techniques previously described.

Once the RBC's are removed, portions of the mixture can be fed to different lines. A first line 202 can be utilized to deliver a first reference sample portion directly to an analyzer 204 via a line 206. As with the above described analyzers, 22 and 44, the characteristics of the cells are sensed by at least two sensing parameters, one of which is a light sensing parameter.

A second line 208 delivers a second sample portion to an "X" cell shifting station 210. As before, the "X" cells are a first WBC population subset of interest which will have at least one sensed cell characteristic modified or shifted in the station 210 to remove the sensed characteristics of the WBC population subset of interest from the sensed cell characteristics of the obscuring WBC population. The sensed cell characteristics are shifted by binding a plurality of non-magnetic microspheres with an antibody specific to the WBC population subset of interest to the cells, as before described. The sample portion then is fed to the analyzer 204. Each of the sets of data obtained by the analyzer 204 can be stored for later comparison in a comparator 212 via a line 214.

In a like manner, a third sample portion is fed to a "Y" cell shifting station 216 via a line 218. The sensed cell characteristics of the "Y" cells are shifted or modified in the station 216 and the sample portion then is fed to the analyzer 204 and the comparator 212. This enables the obtaining of the percentage of the "X" cells and the "Y" cells either directly, or by comparison with the non-shifted results from the line 202. As before, a comparison is not needed and the line 202 can be eliminated in the analyzer 190. This, however, does not enable the obtaining of how many, if any, of the "X" and "Y" cells overlap.

To determine the overlapping percentage, a fourth sample portion is fed to an "X" and "Y" shifting station 220 via a line 222. "Overlapping" is utilized herein to signify that certain cells, populations of cells, subpopulations of cells or formed bodies include at least two receptors or antigens of interest. In this sample portion, both microspheres having an antibody specific to the "X" cells or first WBC population subset of interest and microspheres having an antibody specific to the "Y" cells or the second WBC population subset of interest are combined together. The sample portion then is fed to the analyzer 204 and the data to the comparator 212.

The overlapping percentage is found by adding the separate "X" and "Y" percentage results from lines 208 and 218 together. From this total, the combined "X" and "Y" percentage result from line 222 is subtracted. If the two total percentages are substantially equal, the "X" and "Y" cells do not significantly overlap. If there is a difference, the difference is the percentage overlap of the cells to which both the "X" and "Y" specific microspheres will bind. Although the analyzer 190 has been described having a plurality of lines, the analyzer 190 also can be a sequential analyzer utilizing a single line such as described with respect to the analyzer 50. The plurality of lines also can be provided in accordance with the analyzer 50, utilizing separate mixers 66 for each line 208, 218 and 222 arranged in parallel. Specific results of this procedure are provided in FIGS. 9A–9F.

Figure 9A:
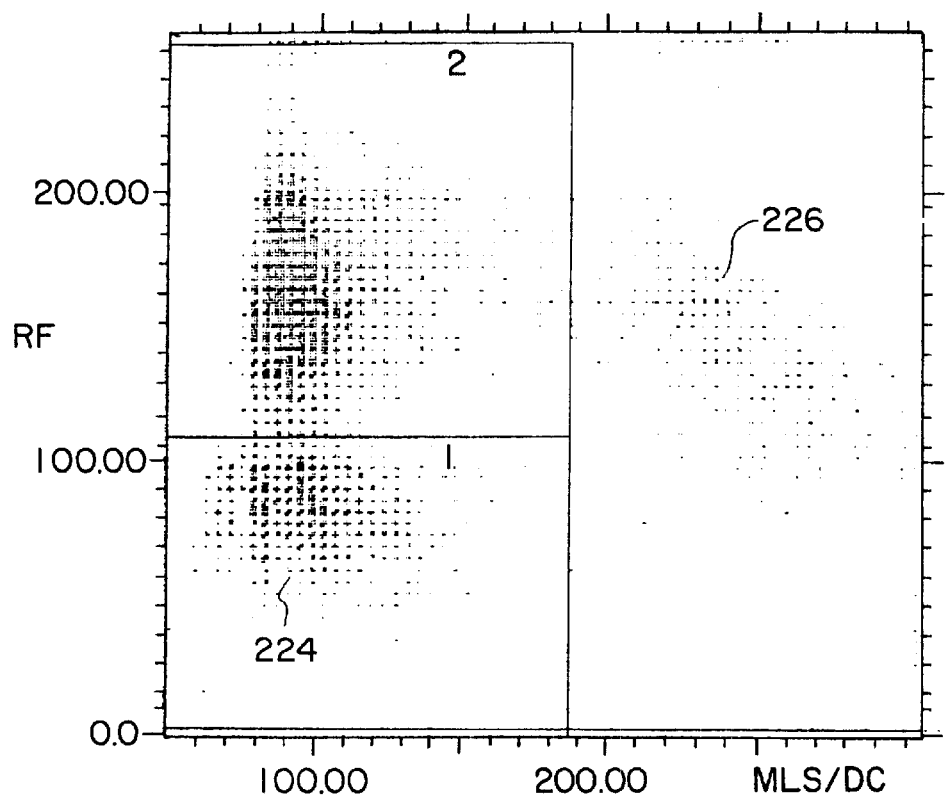
FIGS. 9A–9F are scattergrams of results for overlapping WBC subsets of interest utilizing one of the techniques of the present invention.

FIGS. 9A–9F are scattergrams of specific results obtained utilizing the present invention to determine the overlapping of WBC subsets of interest. FIG. 9A is a scattergram produced by modifying the CD4 subset of interest. As before described with respect to FIGS. 5–7, the CD4 cells are shifted by binding T4 microspheres thereto such as in the station 210. The L's without the shifted group form a grouping 224, while the shifted sensed cell characteristics of the CD4 cells forms a new grouping 226. In this example, the percentage contribution of the CD4 cells was found to be 34.7 percent.

Figure 9B:
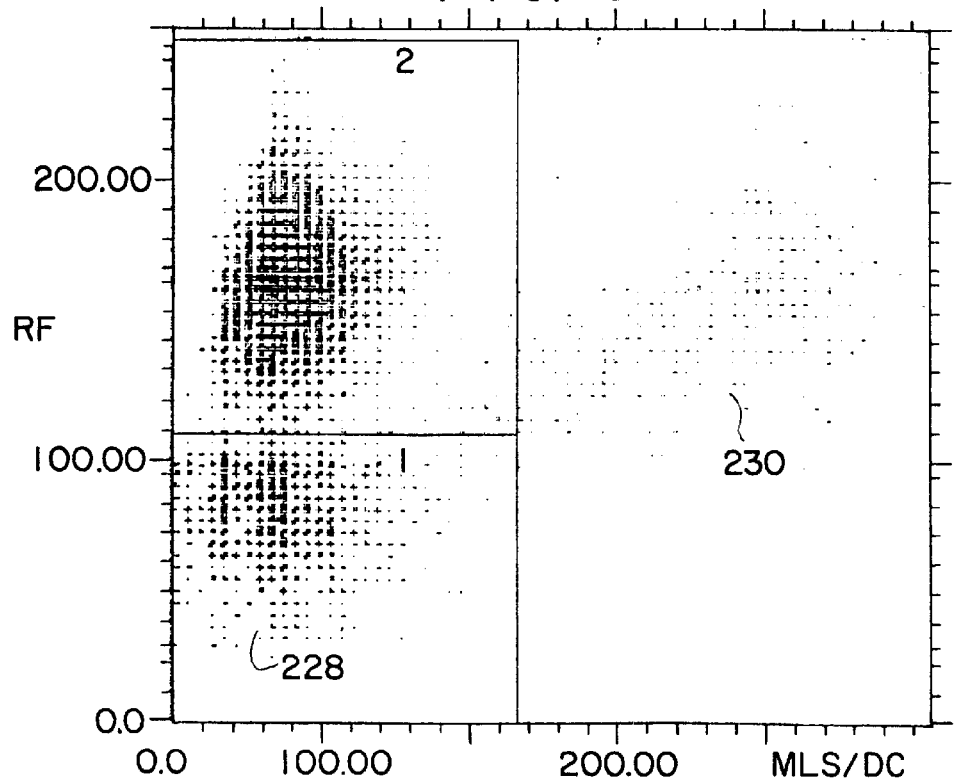

In a like manner, FIG. 9B is a scattergram produced by modifying the CD8 subset of interest such as in the station 216. The remaining L's form a grouping 228, while the shifted sensed cell characteristics of the CD8 cells forms a new grouping 230. In the example, the percentage contribution of the CD8 cells was found to be 33.9 percent.

Figure 9C:
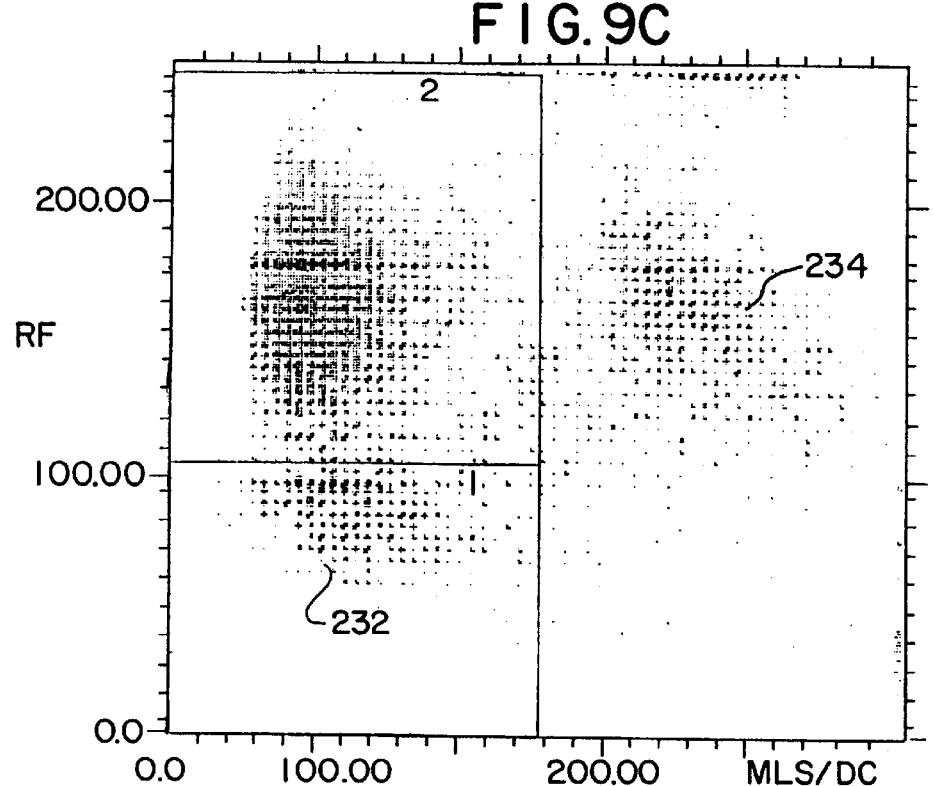

The overlapping CD4 and CD8 cell percentage contribution is illustrated in FIG. 9C by a scattergram produced by modifying the CD4 and CD8 subsets of interest in the same sample portion, such as in the station 220. The remaining L's form a grouping 232, while the shifted sensed cell characteristics of the CD4 and CD8 cells form a new grouping 234. The CD4 and CD8 combined percentage contribution was found to be 70.5 percent. The two separate CD4 and CD8 percentage contributions were 34.7 and 33.9 percent, totalling 68.6 percent. The percentages 68.6 and 70.5 can be compared in the comparator 212 and are substantially the same, showing that the CD4 and CD8 cells do not overlap.

Figure 9D:
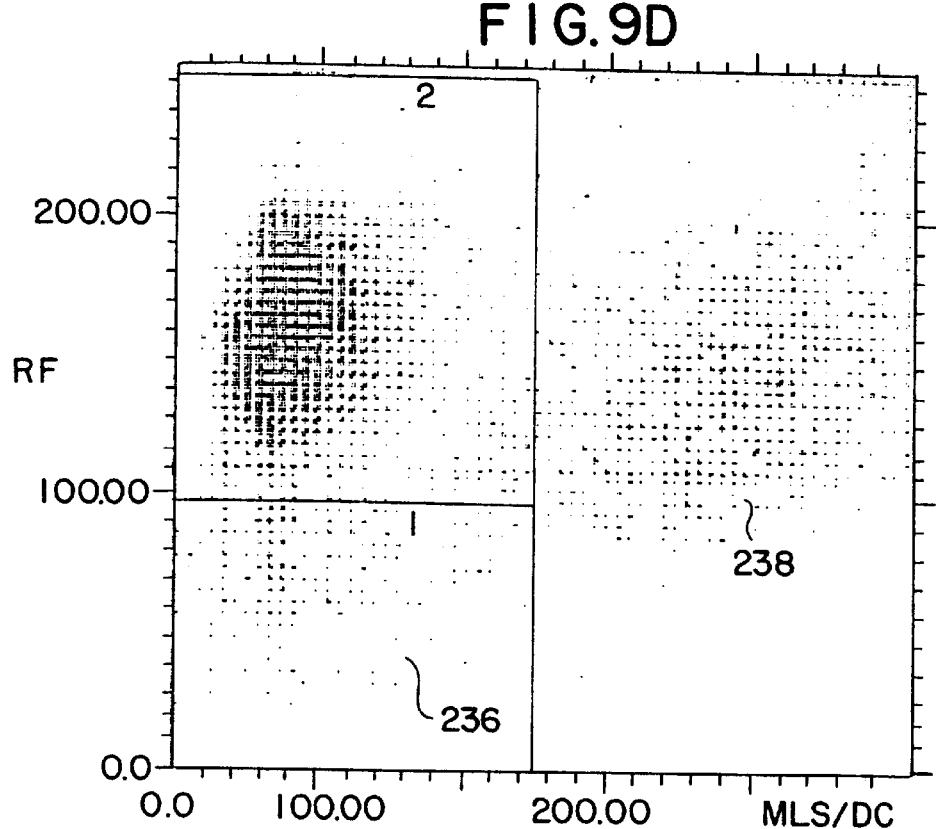

FIG. 9D is a scattergram produced by modifying the CD2 subset of interest, such as in the lines 208 or 218 or in a separate line, not illustrated. The remaining L's form a grouping 236, while the shifted sensed cell characteristics of the CD2 cells form a new grouping 238. The percentage contribution of the CD2 cells was found to be 85.8 percent.

Figure 9E:
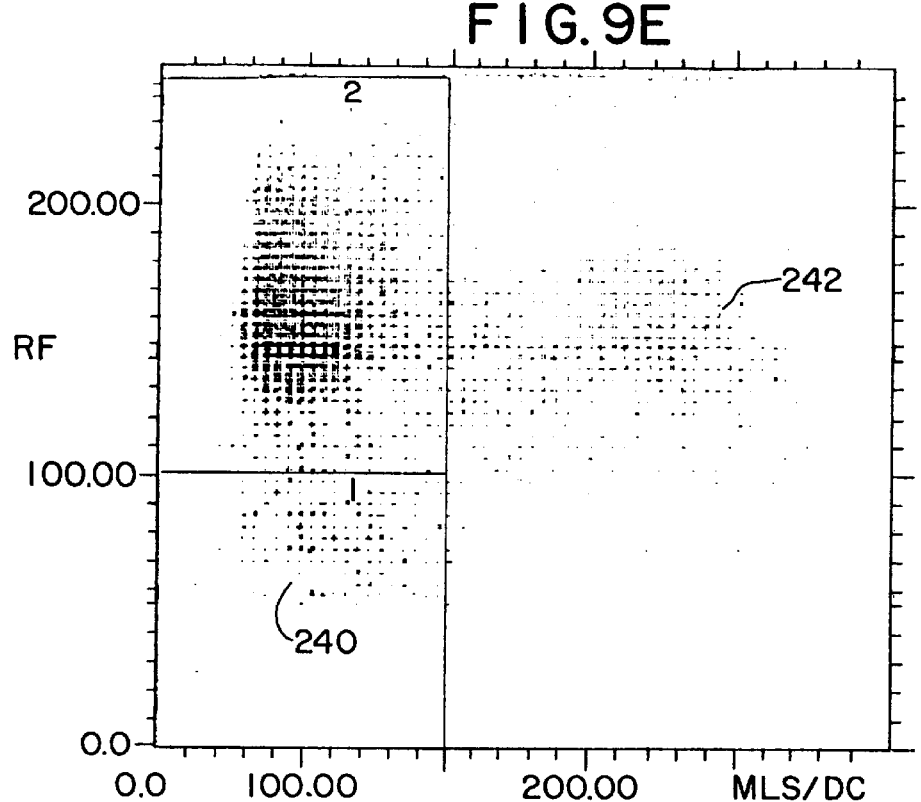

FIG. 9E is a scattergram produced by modifying the CD4 and CD2 subsets of interest in the same sample portion. The remaining L's form a grouping 240, while the overlapping shifted sensed cell characteristics of the CD2 and CD4 cells form a new grouping 242. The CD2 and CD4 cells combined percentage contribution was found to be 88.1 percent. The two separate CD2 and CD4 percentage contributions were 85.8 and 34.7, totalling 120.5 percent, as would be expected. Subtracting 88.1 percent from 120.5 percent leaves a percentage overlap of the CD2 and CD4 cells of 32.4 percent, as would be expected.

Figure 9F:
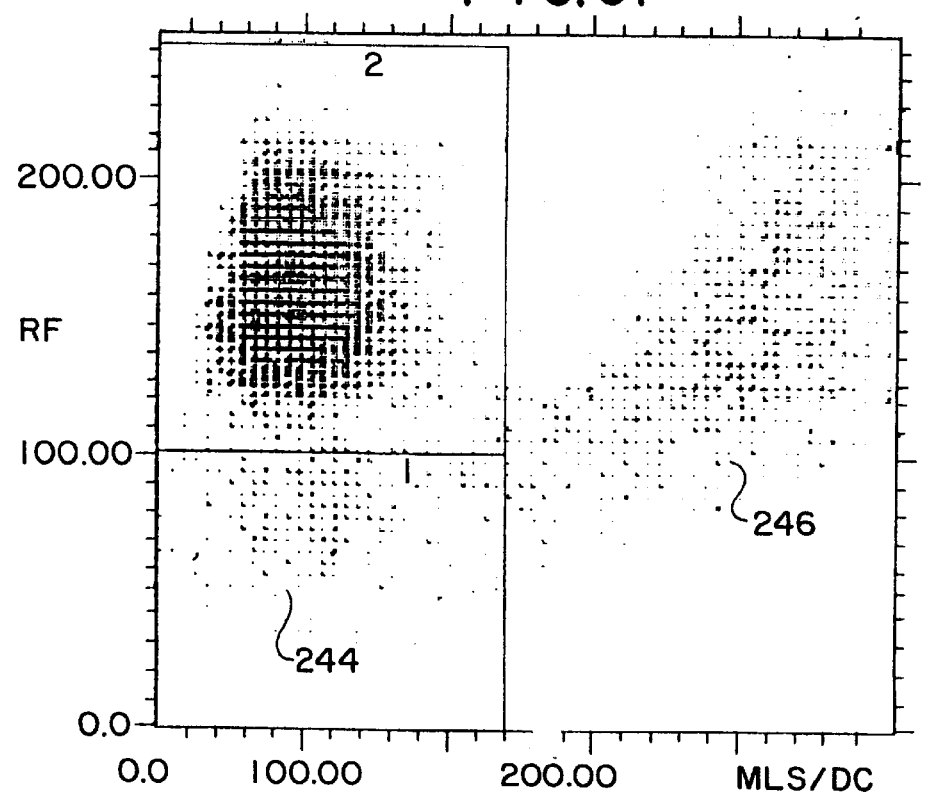

FIG. 9F is a scattergram produced by modifying the CD8 and CD2 subsets of interest in the same sample portion. The remaining L's: form a grouping 244, while the overlapping shifted sensed cell characteristics of the CD2 and CD8 cells form a new grouping 246. The CD2 and CD8 combined percentage contribution was found to be 87.0 percent. The two separate CD2 and CD8 percentage contributions were 85.8 and 33.9, totally 119.7 percent. Subtracting 87.0 percent from 119.7 percent leaves a percentage overlap of the CD2 and CD8 cells of 32.7 percent, again as would be expected.

Figure 10:
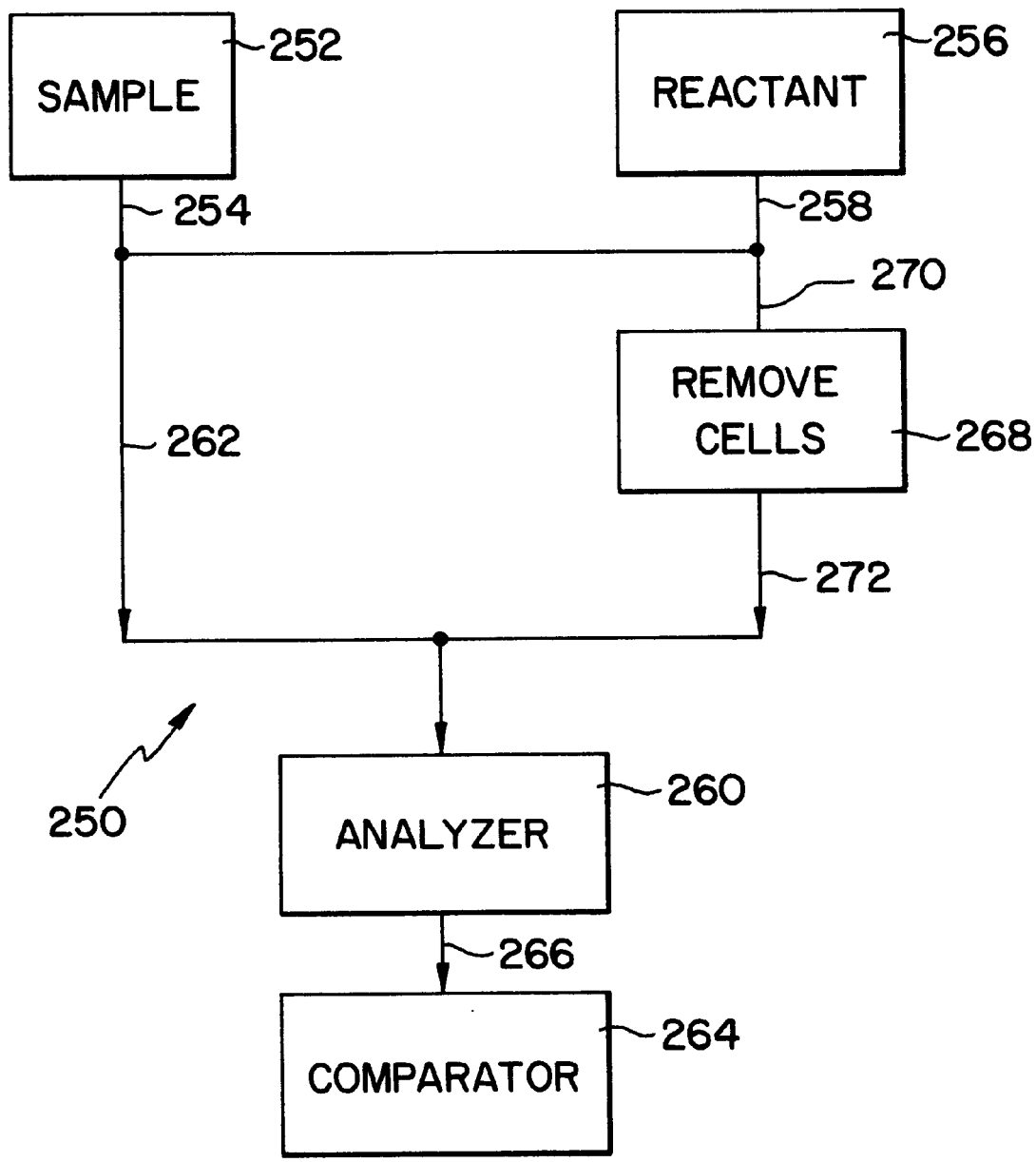
FIG. 10 is a schematic block diagram of a cell screening analyzer embodiment of the present invention for determining obscured cells.

Referring now to FIG. 10, another obscured cell screening analyzer embodiment of the present invention is designated generally by the reference numeral 250. The analyzer 250 includes a sample 252, which contains at least a first set or population of cells (not illustrated). This cell population obscures a cell group of interest, such as a subset or second set of cells, when analyzed as described hereinafter. The sample 252 can include a buffer into which the cells are added.

The sample 252 or a portion thereof is combined via a line 254 with at least one reactant 256 via a line 258. A first portion of the mixture is fed directly to an analyzer 260 via a line 262. The analyzer 260 can be the same as the analyzer 22 and at least senses and counts the number of cells in the sample portion. The results are fed to a comparator 264 via a line 266.

A second sample portion is fed to a cell removing station 268 via a line 270. The cells are removed by shifting or depletion as above described. For shifting, non-magnetic microspheres are bound to the obscuring cell population modifying the sensed cell characteristics sufficiently to remove them from the sensed cell characteristics of the obscured cell population of interest. For depletion, magnetic microspheres are bound to the obscuring cell population which then magnetically are removed from the sample portion.

The second sample portion then is fed to the analyzer 260 via a line 272 and the resulting data is fed to the comparator 264. The data from the two sample portions then is compared to determine the percentage contribution of the obscured cell group of interest.

Figure 11:
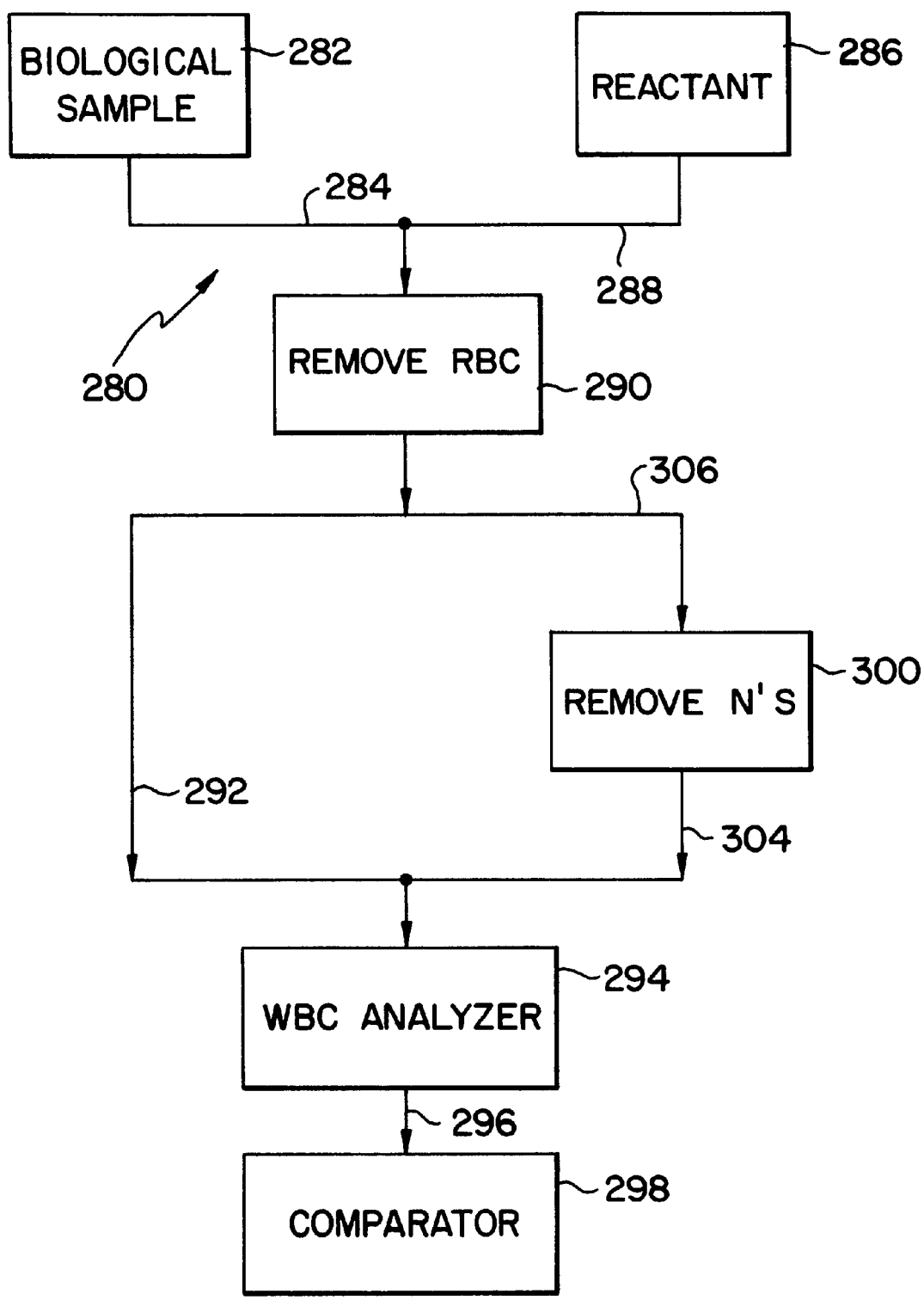
FIG. 11 is a schematic block diagram of another cell screening analyzer embodiment of the present invention for determining obscured cells.

Referring to FIG. 11, another cell screening analyzer embodiment of the present invention is designated generally by the reference numeral 280. The analyzer 280 is similar to the analyzer 250, but includes a biological sample 282 which contains at least a first set of viable biological cells (not illustrated), such as in or from a whole blood sample. The cells of the biological sample 282 are to be involved in a biological reaction in a quantitative and/or qualitative determination or analysis. The biological sample 282 includes at least one WBC population, which WBC population obscures a WBC population of interest. The sample. 282 can also include a buffer into which the cells are added.

The sample 282 or portion thereof is combined via a line 284 with a reactant 286 via a line 288. The RBC's are removed from the sample portion 282 in a RBC removal station 290. The RBC's are removed in one of a number of ways previously described. A portion of the RBC removed sample is fed via a line 292 to an analyzer 294, which again at least senses and counts the WBC population. The data from the analyzer 294 is fed via a line 296 to a comparator 298, as in the analyzer 250.

A second sample portion is fed to a neutrophil (N) functionally designated removal station 300 via a line 302. The N's can be removed from the mixture by shifting or changing one parameter, such as opacity, or by magnetic removal, both as described above. In this example, the particular N specific antibody utilized is disclosed in U.S. Pat. No. 4,931,395, MONOCLONAL ANTIBODY SPECIFIC TO NEUTROPHILS.

The mixture with the N's removed or shifted then is fed to the WBC analyzer 294 via a line 304. The results of the analyzer 294 are fed to the comparator 298. The results of the second sample portion then are compared to the first sample portion to determine if any cells remain in the N area which previously were obscured by the N's.

Figure 12A:
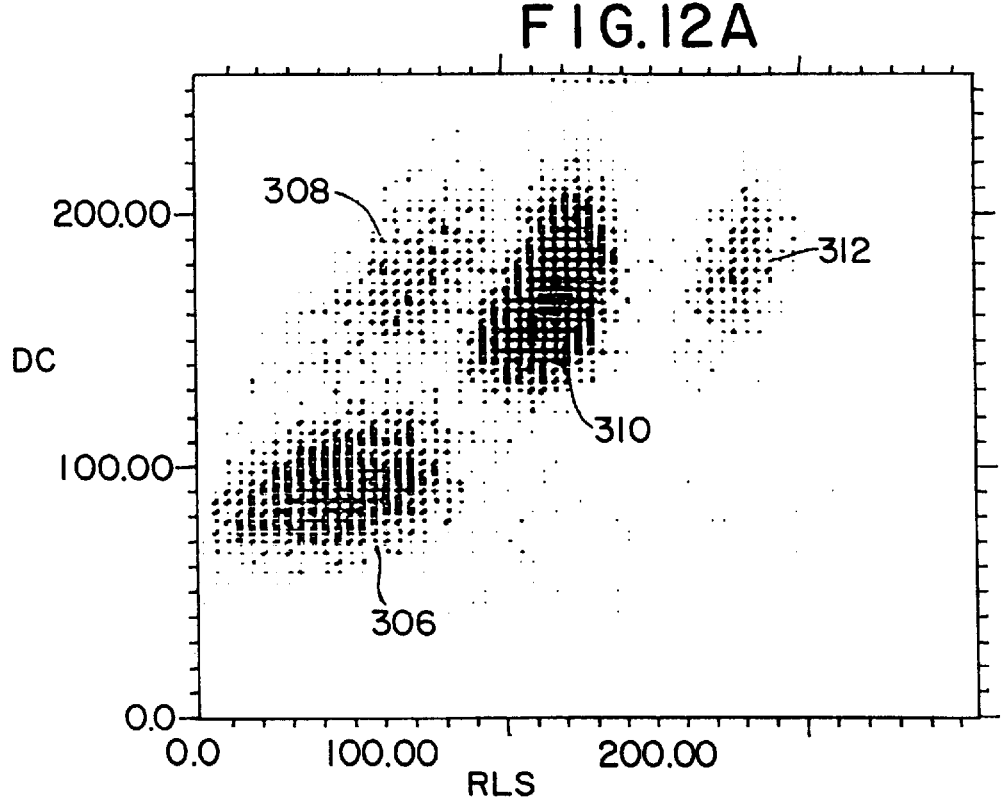
FIGS. 12A and 12B are scattergrams of results of normal blood utilizing light sensing in accordance with the present invention.
Figure 12B:
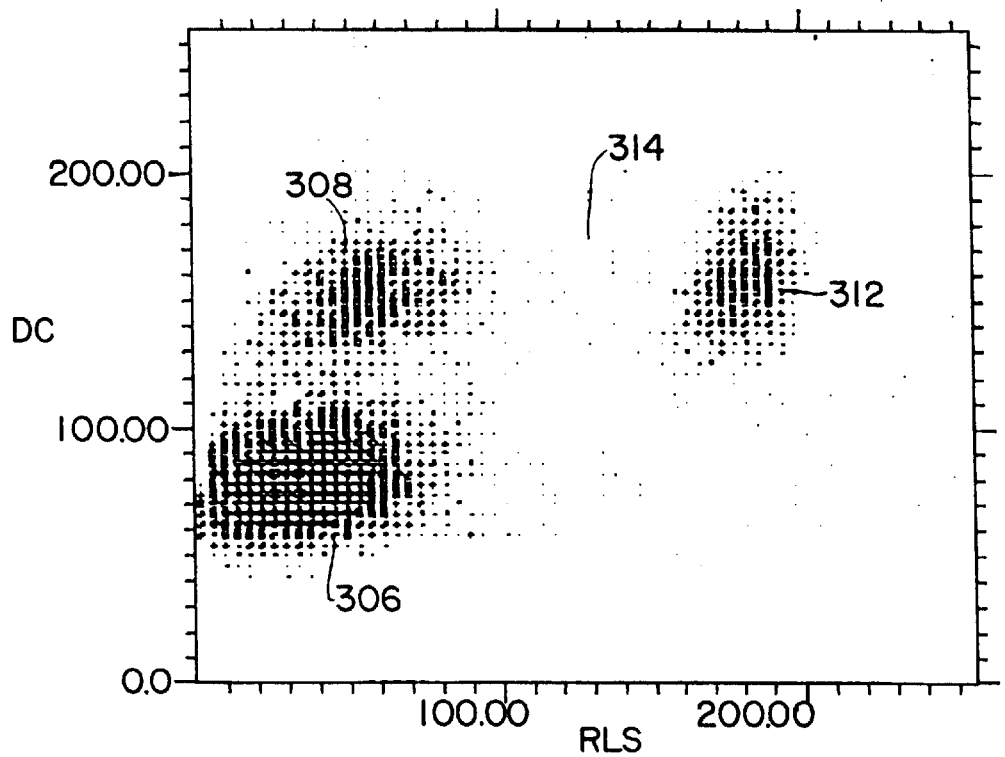

Referring to FIG. 12A, in a normal whole blood sample following elimination of the red blood cells in a VCS type instrument, the light scatter histogram displays population clusters or grouping of the following cell types: L's 306, M's 308, N's 310, and E's 312. However following removal of the mature N's, such as by depletion or shifting, the population clusters are reduced to only three clusters representing the L's 306, E's 312 and M's 308 cell populations as seen in FIG. 12B. The area 314 normally occupied by data representing the mature N population is empty.

Figure 13A:
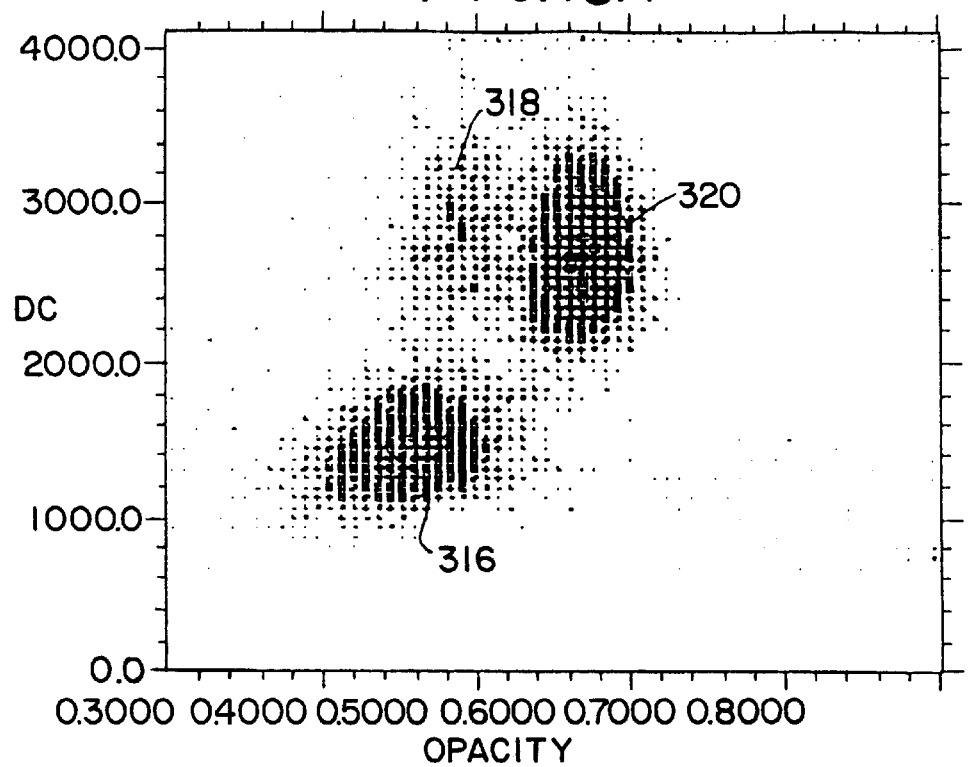
FIGS. 13A and 13B are scattergrams of results of normal blood utilizing only electronic sensing.
Figure 13B:
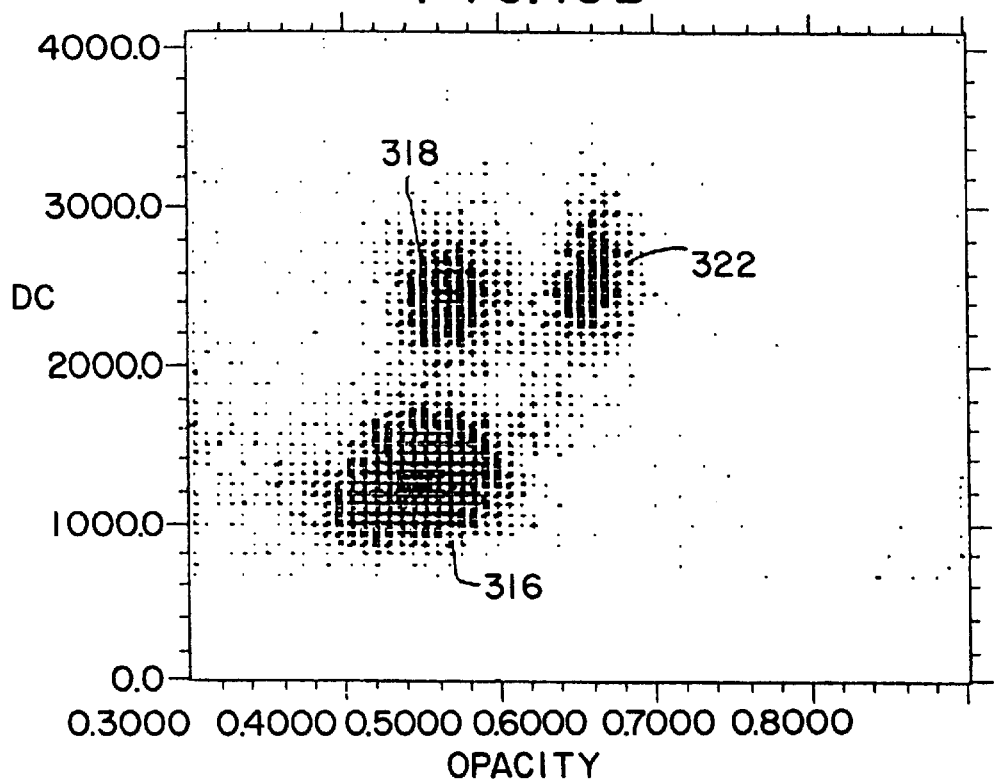

A light sensing parameter is necessary to prevent the E's from obscuring the immature cell area when solely utilizing electronic sensing parameters, as illustrated in FIGS. 13A and 13 B. In FIG. 13A, utilizing DC and opacity as sensing parameters, only three cell groupings can be seen in a normal scattergram. A first grouping 316 is the L's, while a grouping 318 is the M's, but a third grouping 320 contains both E's and N's. Therefore, when the N's are removed, as seen in FIG. 13B, the groups 316 and 318 remain, enhanced by the removal of the N's, but the E's remain in a grouping 322. Any other cells obscured by the N's remain obscured by the E's in the grouping 322.

Figure 14A:
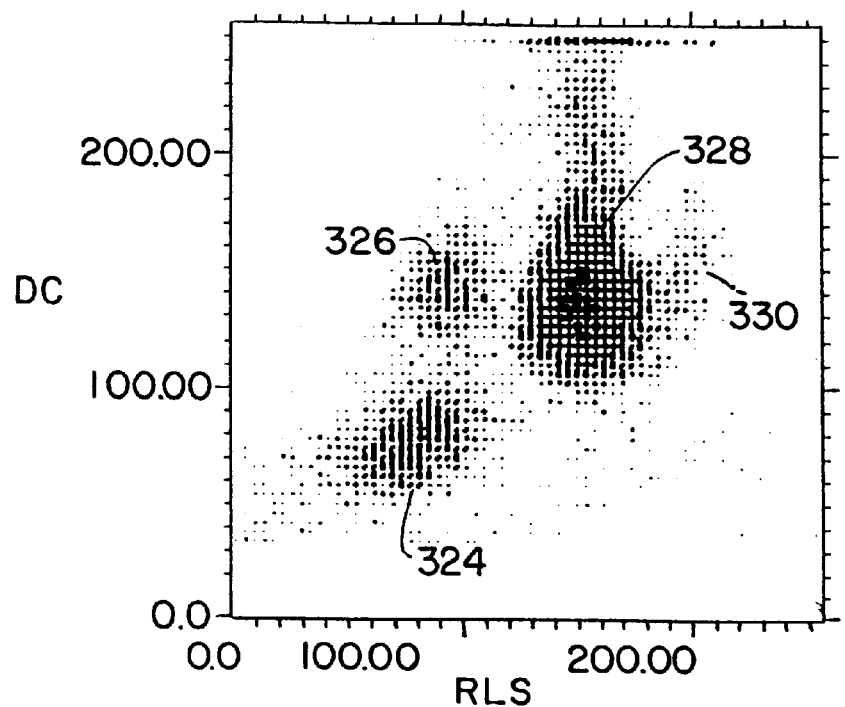
FIGS. 14A and 14B are scattergrams of results of abnormal blood utilizing light sensing in accordance with the present invention.
Figure 14B:
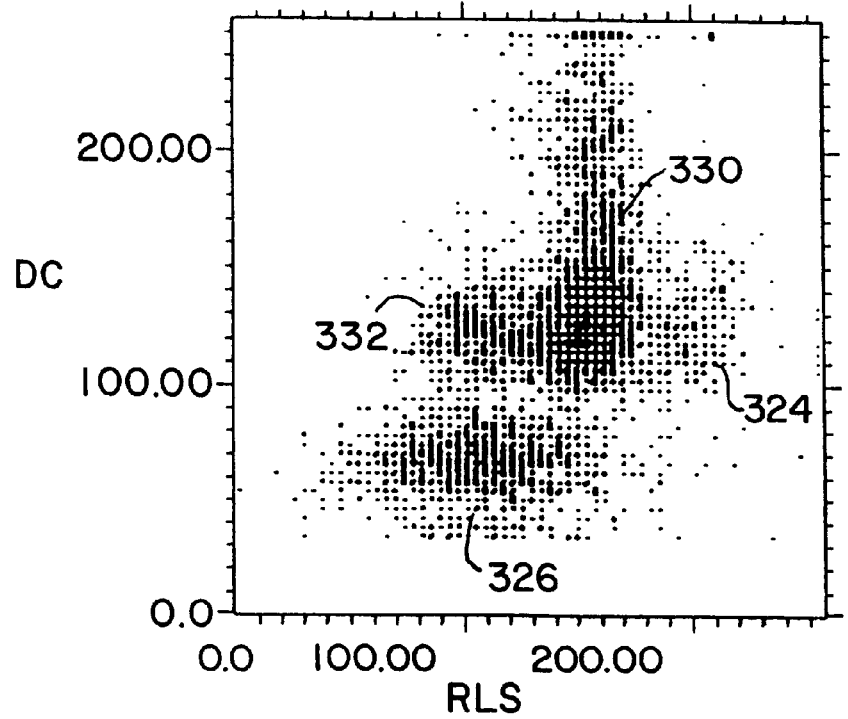
Figure 15A:
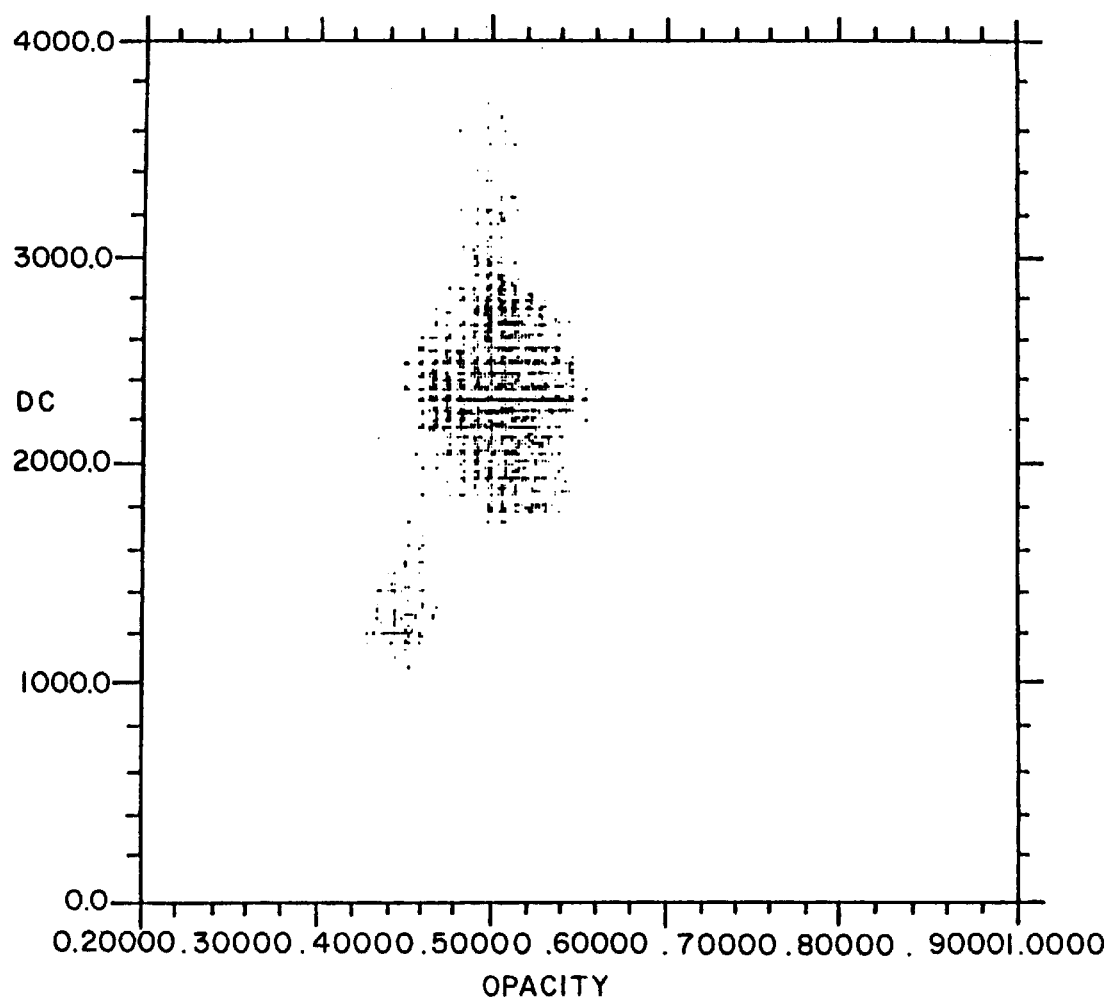
FIGS. 15A and 15B are scattergrams of results of abnormal blood utilizing only electronic sensing.
Figure 15B:
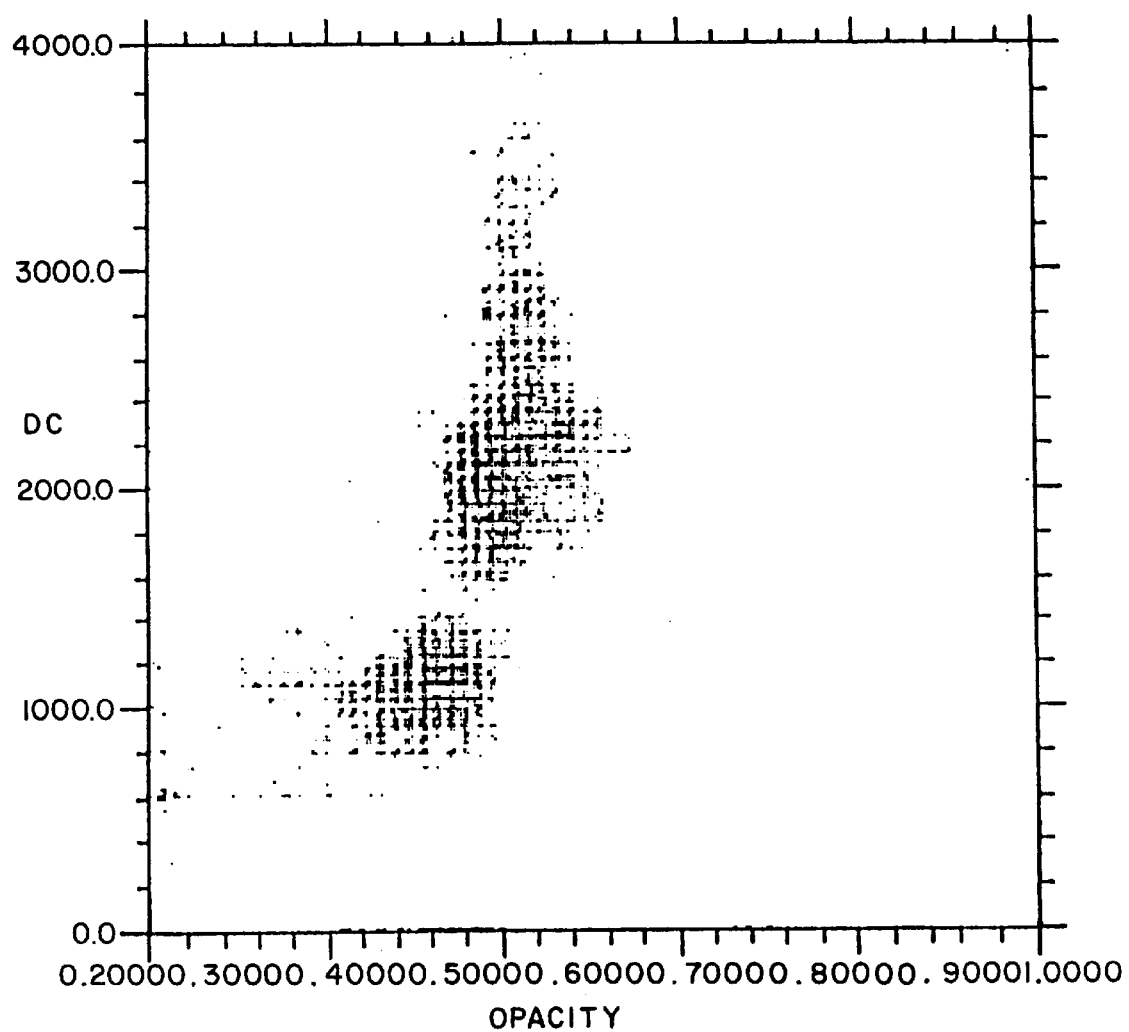

In an abnormal sample as shown in FIGS. 14A and 14B, which contains immature N's, light scatter patterns can be useful in determining the immaturity level of the N's in the sample. FIG. 14A illustrates grouping of L's 324, M's 326, N's 328 and E's 330. Following depletion of the mature N's on such a sample, see FIG. 14B, the N area of the histogram will only display data representing immature N cells 332. An "immaturity index" can then be determined which is indicative of the degree of immaturity of the N's in that sample. The immature N's were calculated from the data in FIGS. 14A and B as representing 36.3 percent of the total WBC's. A manual slide differential was performed on the sample for comparison purposes, which resulted in a total of 37 percent bands, metamyelocytes and myelocytes. The data representing the immature N's again would be obscured by the E's as shown in FIGS. 15A and 15B, when only electronic sensing is utilized.

Figure 16A:
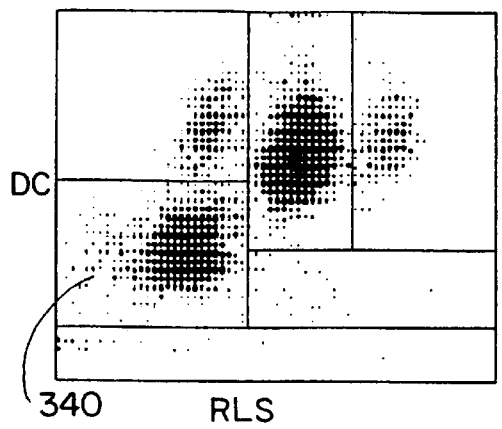
FIGS. 16A–D are scattergrams of results for different WBC subsets of interest utilizing one of the techniques of the present invention.

Although the analyzer 280 was described with respect to removal of N's, the other WBC subsets of interest also can be analyzed as described with respect to FIGS. 16A–D. In these FIGS., the scattergrams are depicted utilizing DC and RLS. FIG. 16A illustrates a control scattergram like that of FIG. 12A, with a L grouping 340.

Figure 16B:
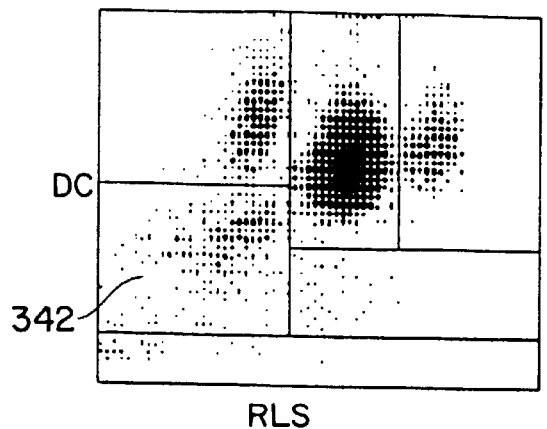

FIG. 16B illustrates a L grouping 342, which depicts the remaining L's after the CD2 WBC subset is removed utilizing magnetic microspheres having a CD2 antibody bound thereto in accordance with the previously described N removal techniques. Comparing the remaining L grouping 342 with the total L grouping 340, results in a CD2 percentage contribution of 89 percent, while a flow cytometry comparison resulted in a percentage contribution of 93 percent.

Figure 16C:
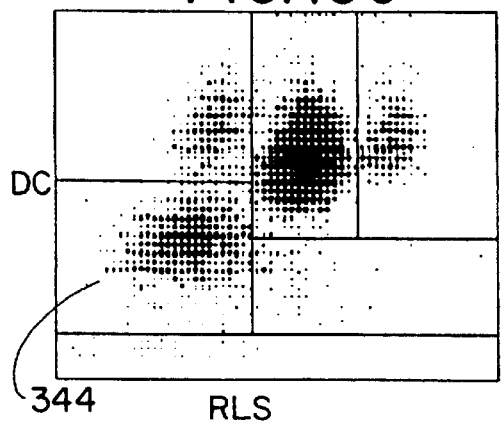

The CD4 depletion results are illustrated by a grouping 344 in FIG. 16C. The CD4 percentage contribution was found to be 58 percent, while the flow cytometry comparison resulted in a percentage contribution of 62 percent.

Figure 16D:
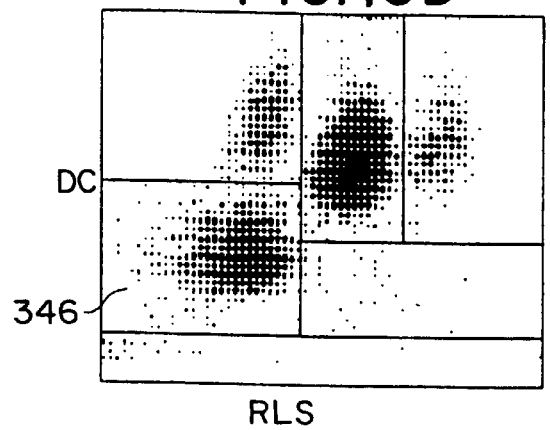

The CD8 depletion results are illustrated by a grouping 346 in FIG. 16D. The CD8 percentage contribution was found to be 21 percent, while the flow cytometry comparison resulted in a percentage contribution of 20 percent.

In practicing the techniques of the invention as previously described, the procedures can be performed in a series of off-line or pre-preparation steps prior to analyzing the sample mixture in an automated analyzer. In the off-line technique, it has been discovered that several precautions must be taken to ensure that the proper results are obtained. These steps and precautions are described with respect to the resulting data illustrated in FIGS. 17A–17D, utilizing CD4 for example purposes. A portion of the same sample is utilized in each figure. The scattergrams are depicted utilizing RF and LS divided by DC.

Figure 17A:
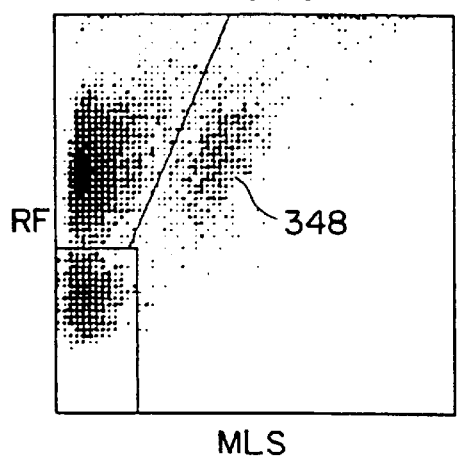
FIGS. 17A–17D are scattergrams of results of various offline preparation techniques.

Referring to FIG. 17A, results of a standard procedure for population modifying or shifting is illustrated. A sample portion of 150 ul of whole blood is combined with 15 ul of CD4 antibody coated microspheres and immediately mixed for two minutes. This results in a CD4 grouping 348 illustrating a proper cell shift and a CD4 percentage contribution of 40.3.

It appears, however, that some variations in this procedure do not allow proper cell modification. The microspheres are provided in the form of microspheres suspended in a liquid reagent. Some of the antibody bound to the microspheres apparently detaches from the microspheres and is free in the suspending fluid or supernatant of the reagent. It appears that this free antibody can bind to and block the antigen sites on the cells to prevent the microspheres from attaching thereto. This results in a partial or total non-shift of the cell group of interest and potentially invalid results. The problem appears not to occur when mixing occurs quickly after combining of the microspheres and the sample. On the other hand, if the microspheres and the sample are combined and allowed to incubate without first mixing, the free antibody will disperse and block the antigen sites.

Figure 17B:
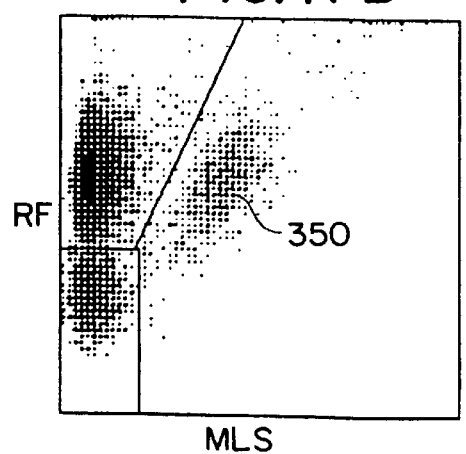

FIG. 17B illustrates the results of combining 15 ul only of CD4 reagent supernatant with the sample, which mixture is allowed to incubate (let stand) for 15 minutes. The microspheres then are added and mixed for two minutes. A CD4 grouping 350 results having a CD4 percentage contribution of 34.4. This decrease of about 6 percent from the grouping 348 illustrates blocking of some of the CD4 cells.

Figure 17C:
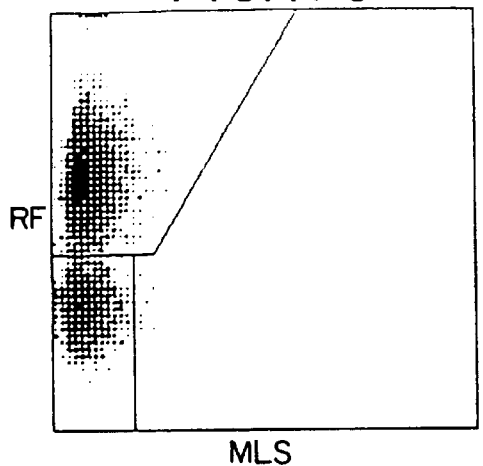
Figure 17D:
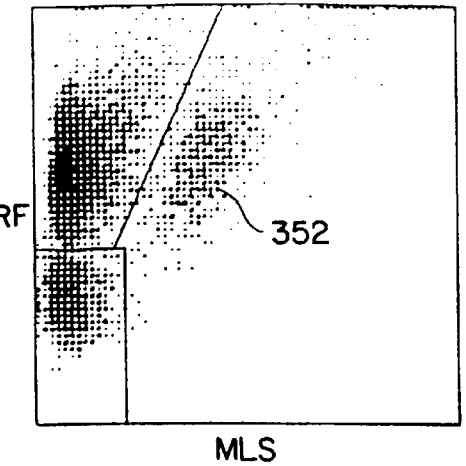

In FIG. 17C, results are illustrated from combining 15 ul of supernatant from the CD4 reagent to the sample portion which is vortexed briefly and then incubated for 15 minutes. The vortexing appears to more rapidly disperse the free antibody, since no shift occurs when the CD4 microspheres then are added and mixed for 2 minutes as before. The results illustrate an insignificant CD4 percentage contribution of 0.5, which results from almost all the cell antigen sites being blocked by the free antibody.

To ensure that only the CD4 antigen sites are being specifically blocked, 15 ul of supernatant from CD8 reagent is added to a sample portion, vortexed and incubated for 15 minutes. The CD4 microspheres then are combined with the sample portion and mixed for 2 minutes. A CD4 cell grouping 352 results, illustrated in FIG. 17D, having a CD4 percentage contribution of 40.0. This illustrates that the CD4 antigen sites are not blocked by the CD8.

In conclusion, in a batch process, the sample portion and microspheres should be mixed immediately or within a few minutes after they are combined. If the sample portion and microspheres are not stirred or vortexed, adequate results should be obtainable for, incubation times of about 10 minutes. The preferable and apparently optimum results are obtained for essentially immediate mixing, especially since once mixed the results do not deteriorate for holding times of at least 1 hour.

Figure 18A:
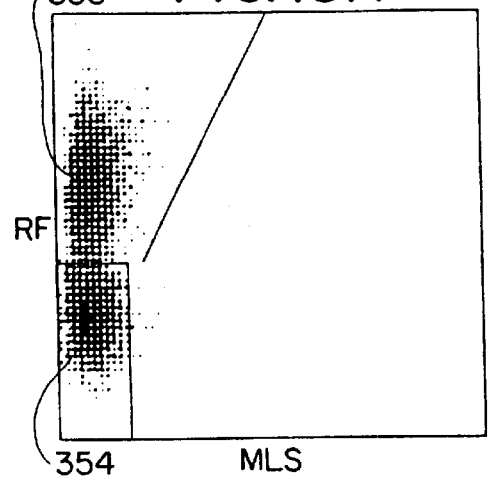
FIGS. 18A–18D are scattergrams of results of utilizing aged blood in accordance with the present invention.
Figure 18B:
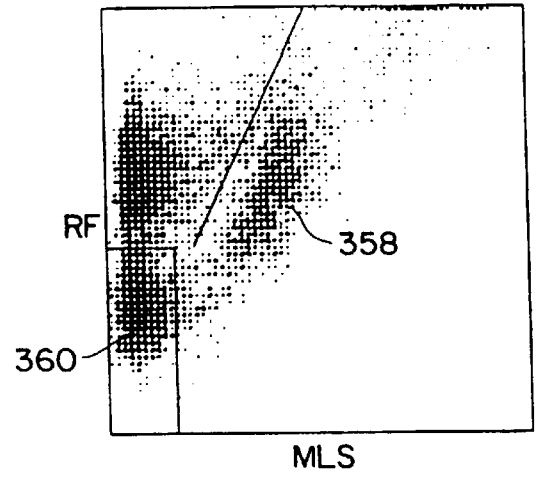

Referring to FIGS. 18A–18D, scattergrams are illustrated similar to those of FIGS. 17A–D for samples which were drawn about twenty four hours before analyzing. In FIG. 18A, two WBC populations are separately enumerated with only the addition of non-binding control microspheres, an L grouping 354 and an M, N and E combined grouping 356. In FIG. 18B, a first WBC subset of interest, the CD4 cells have been shifted by binding T4 microspheres thereto, resulting in a CD4 grouping 358 and a percentage contribution of 43.3. An L grouping 360 results from the L's remaining after the CD4 cells have been shifted away. The CD4 percentage contribution can be found directly, or by relating back to the original groupings in FIG. 18A.

Figure 18C:
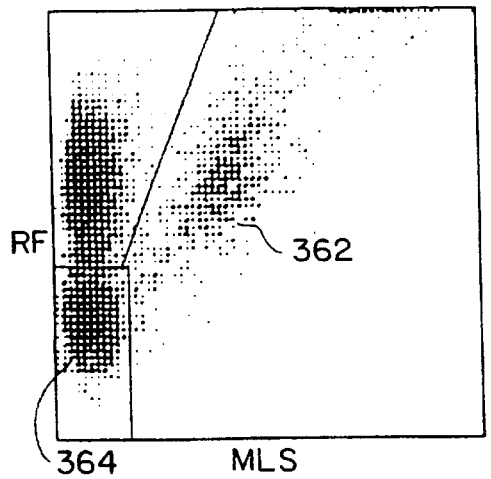
Figure 18D:
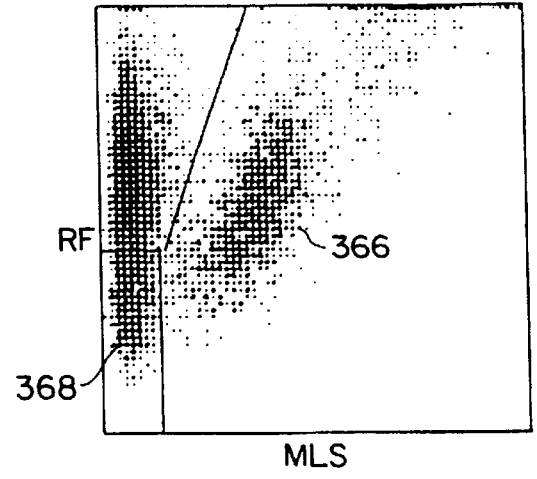

The CD8 and CD2 subset of interest also were obtained as illustrated in FIGS. 18C and 18D respectively. A CD8 grouping 362 resulted in a percentage contribution of 27.6. A remaining L grouping 364 also is formed. A CD2 grouping 366 resulted in a percentage contribution of 65.9. A remaining L grouping 368 also is formed. These aged sample results are important because of the well known fact that blood samples deteriorate with time. These results prove the operability of the present invention with samples up to 24 hours in age. It is of course preferable to utilize the procedure with the least amount of delay (aging) possible, within reason.

Figure 19A:
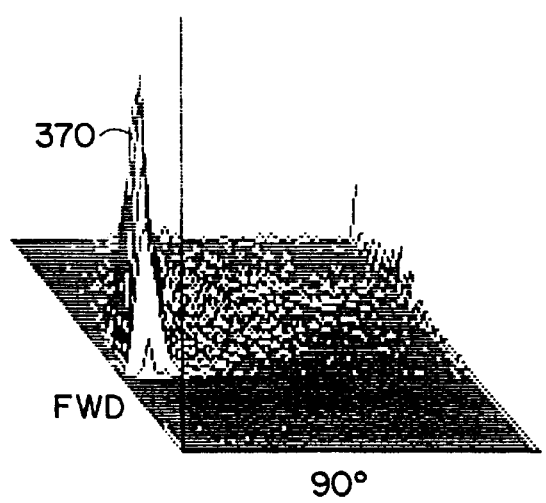
FIGS. 19A–20D are scattergrams of results for different WBC subsets of interest utilizing different sensing parameters in accordance with the present invention.
Figure 19B:
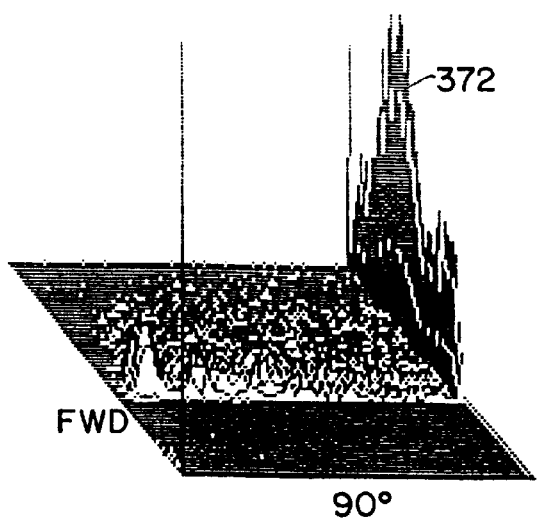
Figure 19C:
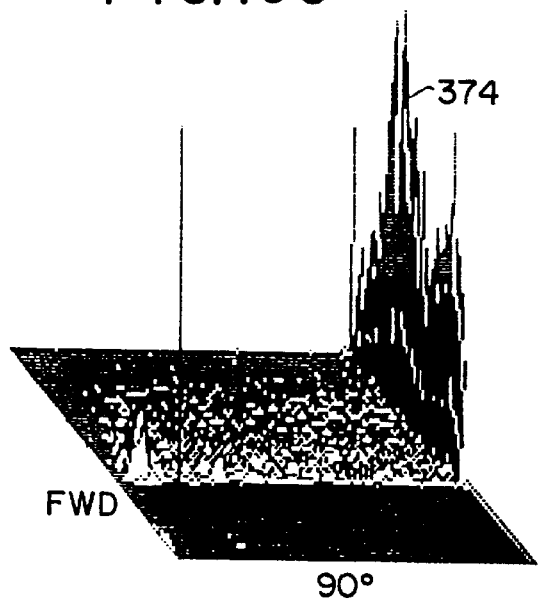
Figure 19D:
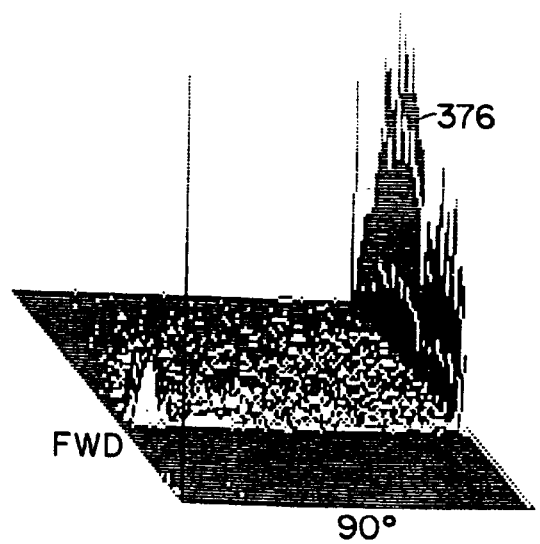

FIGS. 19A–19D and 20A–20D illustrate the shifting of WBC subsets from a sample in which a WBC population first have been isolated from the whole blood sample. In FIG. 19A, a control pattern 370 is obtained which contains all the L WBC populations, utilizing 90 degree light scatter for the X-axis and forward angle light scatter for the Y-axis. In FIGS. 19B–19D, respective CD2 groupings 372, 374 and 376 were obtained utilizing various concentrations of the T11 microspheres, 5, 10 and 25 micrograms, respectively.

Figure 20A:
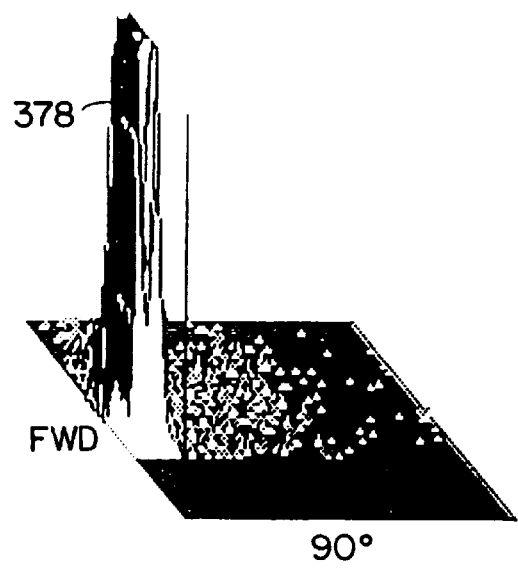
Figure 20B:
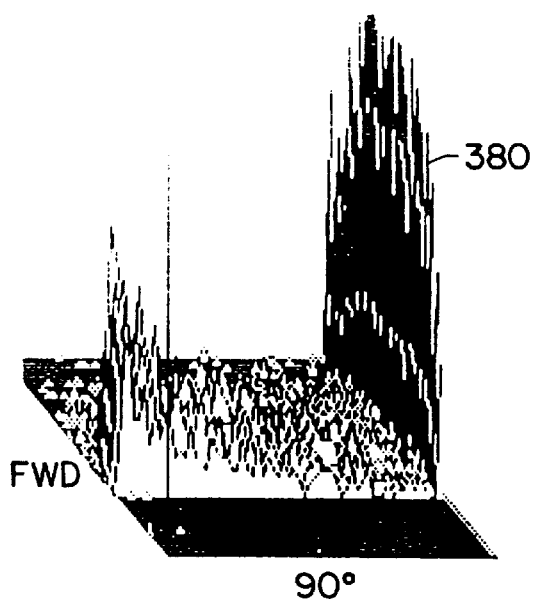
Figure 20C:
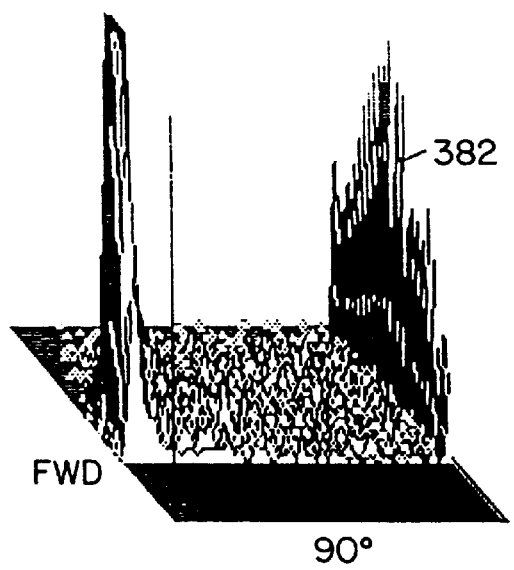
Figure 20D:
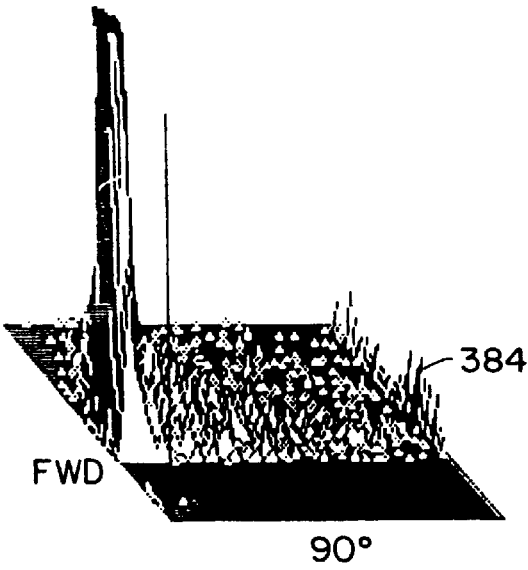

A control pattern 378 again was obtained as illustrated in FIG. 20A. A CD2 grouping 380 was obtained as illustrated in FIG. 20B. A CD4 grouping 382 was obtained as illustrated in FIG. 20C. A CD8 grouping 384 was obtained as illustrated in FIG. 20D.

The analyzers also preferably can compute the absolute number of WBC's and hence also the absolute number of the WBC subset populations. This is especially useful for treatment of persons having AIDS since the specific CD4 population number is utilized in deciding how to perform drug treatment of AIDS patients. The absolute number is found by counting the number of WBC's in a specific volume in a conventional manner as is performed in many commercial cell counting instruments of the assignee, Coulter Electronics, Inc.

When utilizing the techniques of the present invention to magnetically remove microspheres, it is preferable to remove the microspheres before lysing and quenching the sample portion. This is preferred to more efficiently remove the microspheres, which can interfere with the light scatter patterns. Utilizing the 1D3 antibody bound microspheres, for example, the following off-line procedure is preferred:

1. Combine 28 microliters of a whole blood sample with 82 microliters of diluent and 40 microliters of 1D3 microspheres;
2. Mix on the order of 15 seconds;
3. Apply a magnetic field for 1–2 minutes;
4. Remove mixture supernatant;
5. Add 300 microliters lyse for 10–12 seconds;
6. Add 120 microliters quench for 6–8 seconds; and
7. Add sample into system for rest of procedure.

What is claimed is:

1. A method for differentiating first and second subpopulations of blood cells in a blood sample, said first and second subpopulations of blood cells being of similar volume, electrical conductivity and/or light scattering properties, said method comprising the steps of:
   a) providing a plurality of microspheres having a reactant bonded thereto, said reactant specifically binding to a moiety present on only the blood cells of said first subpopulation, said microspheres having a size between about 0.65 and 3.0 microns;
   b) mixing said microspheres with said blood sample to cause a plurality of said microspheres to bind to each of the blood cells of said first subpopulation, whereby a plurality of microsphere/cell complexes are formed in said blood sample; and
   c) differentiating said complexes from unbound blood cells in said blood sample by passing said complexes and unbound blood cells seriatim through a sensing zone while measuring the respective volume, electrical conductivity and light scattering properties of said complexes and blood cells as each passes through said zone.

2. The method as defined by claim 1 wherein said differentiating step comprises producing at least a two dimensional characterization of said complexes and said blood cells representing their respective light scattering and electrical properties.

3. The method as defined by claim 1 wherein said light scattering property is measured by irradiating each of said complexes and unbound blood cells as it passes through said zone with a beam of radiation and measuring the intensity of scattered light between 10 and 70 degrees with respect to the direction of said beam of radiation.

4. The method as defined by claim 1 wherein said electrical conductivity is measured by subjecting said complexes/unbound cells to an RF electric field.

5. A method for differentiating first and second subpopulations of blood cells in a blood sample, said first and second subpopulations of blood cells being of similar volume, electrical conductivity and/or light scattering properties, said method comprising the steps of:
   a) providing a plurality of microspheres having a reactant bonded thereto, said reactant specifically binding to a moiety present on only the blood cells of said first subpopulation, said microspheres having a size between about 0.65 and 3.0 microns;

b) mixing said microspheres with said blood sample to cause a plurality of said microspheres to bind to each of the blood cells of said first subpopulation, whereby a plurality of microsphere/cell complexes are formed in said blood sample; and c) differentiating said complexes from unbound blood cells in said blood sample by passing said complexes and unbound blood cells seriatim through a sensing zone and at which each of said complexes and unbound blood cells is irradiated by a beam of light and subjected to an electrical field, whereby the respective volume and/or electrical conductivity of said complexes and unbound blood cells can be determined substantially simultaneously with the light scattering properties as each complex and unbound blood cell passes through said zone.

6. The method as defined by claim 5 wherein said differentiating step comprises producing at least a two dimensional characterization of said complexes and unbound blood cells representing their respective volumes and light scattering properties.

7. The method as defined by claim 5 wherein said differentiating step comprises producing at least a two dimensional characterization of said respective electrical conductivities and light scattering properties.

8. The method as defined by claim 5 wherein said light scattering property is measured by irradiating each of said complexes and unbound blood cells as it passes through said zone with a beam of radiation and measuring the intensity of scattered light between 10 and 70 degrees with respect to the direction of said beam of radiation.

9. The method as defined by claim 5 wherein said volume is determined by subjecting each of said complexes and unbound cells to a DC electric field while said cell passes through said sensing zone.

10. The method as defined by claim 5 wherein said electrical conductivity is determined by subjecting each of said complexes and unbound cells to an RF electric field as each of said complexes and unbound cells passes through said sensing zone.

11. The method as defined by claim 5 wherein said first and second subpopulations of blood cells are lymphocytes, and wherein said first subpopulation of lymphocytes are of a type selected from the group consisting of CD2, CD4 and CD8 cells.

* * * * *